United States Patent
Braman et al.

(10) Patent No.: US 6,825,330 B2
(45) Date of Patent: Nov. 30, 2004

(54) COMPOSITIONS AND METHODS USING PLATINUM COMPOUNDS FOR NUCLEIC ACID LABELING

(75) Inventors: Jeffrey Braman, Carlsbad, CA (US); Haoqiang Huang, San Diego, CA (US)

(73) Assignee: Stratagene California, La Jolla, CA (US)

(*) Notice: Subject to any disclaimer, the term of this patent is extended or adjusted under 35 U.S.C. 154(b) by 0 days.

(21) Appl. No.: 10/086,515

(22) Filed: Mar. 1, 2002

(65) Prior Publication Data

US 2002/0165369 A1 Nov. 7, 2002

Related U.S. Application Data

(60) Provisional application No. 60/272,921, filed on Mar. 2, 2001.

(51) Int. Cl.[7] .................. C07H 21/00; C07H 21/02; C07H 21/04
(52) U.S. Cl. ............... 536/23.1; 536/24.3; 536/26.6
(58) Field of Search ............... 536/23.1, 26.6, 536/24.3

(56) References Cited

U.S. PATENT DOCUMENTS

| | | | |
|---|---|---|---|
| 4,207,416 A | 6/1980 | Hoeschele | 536/23 |
| 4,569,932 A | 2/1986 | Bergquist et al. | 514/185 |
| 4,843,161 A | 6/1989 | Lippard et al. | 546/10 |
| 5,580,990 A | 12/1996 | van den Berg et al. | 549/212 |
| 5,714,327 A | 2/1998 | Houthoff et al. | 435/6 |
| 5,985,566 A | 11/1999 | Houthoff et al. | 435/6 |

FOREIGN PATENT DOCUMENTS

| | | | |
|---|---|---|---|
| EP | 0539466 B1 | 7/1991 | C07F/15/00 |
| WO | WO92/01699 | 2/1992 | C07F/15/00 |
| WO | WO96/35696 | 11/1996 | C07F/15/00 |
| WO | WO 98/15564 | 4/1998 | C07F/15/00 |

OTHER PUBLICATIONS

Fichtinger-Shepman, et al. "Adducts of the antitumor drug cis-Diamminedichloroplatinum (II) with DNA: formation, Identification, and Quantitation" *American Chemical Society* 1985, V. 24 p. 707–713.

Eremenko, et al., "Imido/Nitrene Ligands in the Complexes of Platinum Metals", Journal of Organometallic Chemistry. 1998, vol. 551. pp. 171–194.

Copy of the International Search Report (PCT/US02/06410).

*Primary Examiner*—Jezia Riley
(74) *Attorney, Agent, or Firm*—Kathleen M. Williams; Palmer & Dodge, LLP

(57) ABSTRACT

The invention relates to novel platinum-based compounds for labeling biomolecules. Platinum based labeling compounds according to the invention irreversibly attach to a target biomolecule via coordination of a platinum (II) metal center with N or S atoms on the target biomolecule. The invention relates to the novel compounds themselves, methods of making the platinum-based labeling compounds, probes labeled with such compounds, methods of making such labeled probes, and kits comprising the novel platinum-based labeling compounds and/or probes labeled with them. The invention also relates to methods of using probes labeled with platinum-based labeling compounds of the invention, particularly array and microarray hybridization methods.

104 Claims, 13 Drawing Sheets

A square-planar 4-coordination Pt $^{2+}$complex   cis-Pt-DDP   trans-Pt-DDP $d^{14}$ electronic configuration is the rule The Pt(II) ion coordinated to N⁷ of a guanine DNA base.

cis-DDP interactions with DNA.

DNA interstrand crosslink

DNA intrastrand crosslink

DNA-protein crosslink (mono-functional)

A. cDNA labeled with allyl-amine dUTP/Cy3-NHS
B. cDNA labeled with cis-Pt-Cy3
C. cDNA labeled with 5'-Cy3 primer

COMPOSITIONS AND METHODS USING PLATINUM COMPOUNDS FOR NUCLEIC ACID LABELING

RELATED APPLICATION

This application claims the benefit of U.S. Provisional Application No. 60/272,921, filed on Mar. 2, 2001. The entire teachings of the prior application are incorporated herein by reference.

BACKGROUND OF THE INVENTION

Labeled biomolecules are essential to a wide array of methods used for biological research, medical diagnosis and therapy. Labeled biomolecules permit a researcher or clinician to detect the location, size, amount or other properties of biomolecules of interest. Commonly labeled biomolecules include, among others, nucleotides, oligonucleotides, nucleic acids, amino acids, peptides and polypeptides, proteins, carbohydrates and lipids.

Nucleic acid hybridization is one of the most frequently used methods requiring labeled nucleic acid probes, and is used in both research and diagnostic medicine. Methods utilizing nucleic acid hybridization include, for example, fluorescent in-situ hybridization (FISH), DNA in-situ hybridization (DISH; Singer & Ward, 1982, Proc. Natl. Acad. Sci. U.S.A. 79: 7331–7335), RNA in-situ hybridization (RISH; Singer et al., 1986, BioTechniques 4: 230–250), multi-color fluorescent in-situ hybridization (MFISH), gene mapping (Pitta et al., 1990, Strategies 3: 33), Southern and Northern blots (Southern, 1975, J. Mol. Biol. 98: 503–517; Alwine et al., 1977, Proc. Natl. Acad. Sci. U.S.A. 74: 5350–5354), microarray-based assays (Callow et al., 2000, Genome Res. 10: 2027–2029) and diagnostic array assays, among others. Radioisotopes are perhaps the most commonly used detectable labels for nucleic acid hybridization. However, there is a need in the art for non-isotopic alternatives to radiolabeling because isotopic labels are expensive, dangerous to handle and have increasingly expensive disposal costs.

An ideal non-radioactive labeled probe for nucleic acid hybridization should have the following properties: 1) label that is easily attached to the probe; 2) stability under various separation/purification conditions such as gel electrophoresis, HPLC, TLC or column purification; 3) stability under nucleic acid hybridization conditions, such as exposure to solutions containing detergents and formamide, and temperatures up to 100° C.; 4) label that does not interfere with hybridization to a complementary target; 5) label that is detectable at very low amounts, ideally 1 attomole of nucleic acid or less; 6) applicability to solution or solid-phase hybridization assays such as those performed on membranes, microtiter plates and microarrays (gene chips); 7) adaptability to homogeneous assay formats wherein the hybridized probe is detectable and distinguishable from unhybridized probe in solution; 8) long shelf-life for storage; and 9) compatibility with automated analysis and high throughput instruments.

Enzymatic Labeling Methods

Labels are generally attached to nucleic acids using either enzymatic or chemical means. Enzymatic methods are useful for both end-labeling of existing strands of nucleic acid and for the template-dependent internal labeling of nucleic acid strands polymerized in vitro or in vivo. There are several different approaches taken to the enzymatic generation of end-labeled nucleic acid probes. Polynucleotide kinase is often used to label the 5' end of a polynucleotide strand with a radioactive phosphate (e.g., $^{32}P$ or $^{33}P$) transferred from the gamma position of labeled ATP. Kinase labeling results in, at best, a single radioactive phosphate label moiety per polynucleotide strand. Alternatively, end-labeled probes comprising more than one label moiety per strand can be generated by a 3'-tailing reaction catalyzed by terminal transferase (Roychoudhury et al., 1980, Nucleic Acids Res. 6: 1323–1333). However, the optimal reaction conditions vary for the incorporation of the various nucleotides by terminal transferase, and conditions vary for each different probe to be labeled. Another alternative for end-labeling probes is to use PCR to make 5' end-labeled DNA probes through incorporation of a 5'-labeled primer. This approach can rapidly generate a significant quantity of extended, end-labeled probes. However, the PCR method requires first generating the end-labeled primer at high specific activity.

There are also a number of approaches for generating internally labeled probes using enzymes. One of the commonly used enzymatic techniques is "Random-Primed" labeling, (Feinberg & Vogelstein, 1983, Anal. Biochem. 132: 6–13; Feinberg & Vogelstein, 1984, Anal. Biochem. 137: 266–267). The resulting labeled probe is a mixture of different sized sequences of the template. The ratio between primer and template, and the amount of labeled and unlabeled nucleotide are varied to obtain the highest specific activity probes. An alternative internal labeling method is "Nick Translation" (Rigby et al., 1977, J. Mol. Biol. 133: 237–251). In this procedure, a mixture of the endonuclease Dnase I and 5'→3' DNA polymerase Pol I is used, and the ratio of these two enzymes and the percentage of labeled nucleotide determines the amount and length of the labeled DNA. Another alternative for generating an internally-labeled probe is the Polymerase Chain Reaction (PCR; Mullis et al., 1986, Cold Spring Harb. Symp. Quant. Biol. 51 Pt. 1: 263–273), performed in the presence of a mixture of labeled and unlabeled nucleotides. For mRNA analysis, reverse transcription (RT) in the presence of labeled deoxyribonucleotides is the traditional method to create labeled cDNA (Varmus & Swanstrom, 1979, in *Molecular Biology of Tumor Viruses*, vol.2: *RNA Tumor Viruses* (Weiss et al., Eds) pp. 369–512, Cold Spring Harbor Press, Cold Spring Harbor, N.Y.).

In any enzymatic labeling method, the reaction conditions and the ratio of labeled to unlabeled nucleotides should be optimized for every labeling reaction, thereby complicating the labeling procedure. Each of the enzymatic labeling methods described above, and other enzymatic methods known to those skilled in the art, tend to work well for the incorporation or attachment of radiolabeled species. In general, isotopic labels do not interfere with the function of the enzymes to label nucleic acids. In contrast, labeling moieties other than isotopes tend to be large and can interfere with the labeling reactions, such that relatively poor incorporation rates and low total incorporation of the label is observed. The relatively poor recognition and incorporation of nucleotides labeled with non-isotopic moieties, such as fluorescent molecules, can sometimes be compensated by increasing the absolute concentration and modifying the ratio of the labeled nucleotide in the reaction. However, even when this approach works, the cost of the labeling reaction is increased. In addition, variation in enzyme quality, resulting for example from storage or frequent freeze/thaw cycles, can result in variable labeling reaction efficiency.

A common alternative solution to the problem of poor incorporation of nucleotides labeled with larger non-isotopic markers is to enzymatically incorporate a nucleotide modified with a small affinity moiety, such as biotin or digoxigenin, into a probe sequence. The probe may then either be directly reacted with a labeled affinity binding partner, such as avidin or anti-digoxigenin antibodies, or it may be hybridized to target nucleic acid and then reacted with a labeled affinity binding partner. The biotin/avidin system is characterized by subpicogram sensitivity (Feinberg & Vogelstein, 1983, supra; Feinberg & Vogelstein, 1984, supra). A disadvantage of this method is its high non-specific background due to the inherent positive charge exhibited by avidin at neutral pH and the endogenous ubiquity of vitamin H (biotin) in biological samples. This method also suffers from problems discussed above related to variations in enzyme activity leading to variable labeling reaction efficiency.

Chemical Labeling Methods

Chemical labeling methods are an alternative to the enzymatic labeling methods. Among methods for direct derivatization of nucleic acids with detectable markers are photolabeling reactions using aryl azide compounds (Forster et al., 1985, Nucleic Acids Res. 13: 745–761) psoralen, angelicin, acridine dyes (Chimino et al., 1985, Ann. Rev. Biochem. 54: 1151–1193), or direct intercalation with detectable dyes such as ethidium bromide or fluoren derivatives (Al-Hakeem & Hull, 1986, Nucleic Acids Res. 14: 9965–9976). These methods are limited by low labeling efficiency and some of the labeling compounds are toxic.

Alternative chemical labeling methods are available in which detectable haptens are introduced into the DNA probe via an activated linker arm. Primary modification of the nucleic acids is obtained either by transamination (Viscid et al., 1986, J. Clin. Microbiol. 23: 311–317), mercuration (Dale et al., 1975, Biochemistry 14: 2447–2457), bromination, thiolation, or amine substitution with bifunctional reagents, followed by coupling with activated linker arms carrying a detectable hapten. For example, allylamine moieties can be introduced into DNA probes by mercuration/substitution (Id.) or by enzymatic incorporation of an allylamine modified nucleotide. The allylamine tethered probe can then react with the N-hydroxysuccinimide (NHS) ester of biotin or a fluorescent dye (Langer et al., 1981, Proc. Natl. Acad. Sci. U.S.A. 78: 6633–6637; Hopman et al., 1986, Nucleic Acids Res. 14: 6471–6488). For the enzymatic incorporation of allylamine-modified nucleotides, one needs to optimize the ratio of the allylamine dNTP and unmodified dNTP. In addition, the coupling yield of an allylamine tagged probe with dye-NHS ester may be reduced due to the instability of dye-NHS ester in water (Molecular Probes, 1997, Product Information, Amine-Reactive Probes). The half-life of dye-NHS ester in aqueous solution at neutral pH is approximately 10–20 minutes, and is even shorter under conditions generally used for the coupling reaction (e.g., pH 8.5–9.1). As an alternative, chemical labeling of oligonucleotides can also be performed internally or at both termini during automated oligonucleotide synthesis by incorporation of protected allylamine synthetic components which are then reacted with NHS esters of haptens of interest (Haralambidis et al., 1987, Nucleic Acids Res. 15: 4857–4867). The degree of labeling is limited due to the short length of synthetic oligonucleotides.

The complexity of the DNA labeling methods described above not only related to enzyme and dye-NHS ester instability, but also because multiple steps are required to optimize the labeling reaction conditions. There is a need to develop a simple reliable method to make labeled DNA probes with high efficiency.

Chemical Labeling Methods Using Platinum Compounds

Platinum (atomic number 78, atomic weight 195) is a transition metal with an outer electronic configuration of $4f^{14}5d^{9}6s^{1}$. As a d-block metal, $Pt^{(II)}$ tends to gain an additional four electrons to form a square-planar four coordination $Pt^{(II)}$ complex (FIG. 1; Cotton et al. in *Advanced Inorganic Chemistry* ($6^{th}$ ed), John Wiley & Sons, Inc., NY, pp. 1063, 1072, 1076). In this complex, the $Pt^{(II)}$ ion acts as an electron acceptor (Lewis acid), showing a high affinity for "soft" ligands such as heavier halogens, phosphines, sulfides, nitrogen compounds, alkenes, alkynes, and other π-bond compounds.

FIG. 1 also shows the structures of cis- and trans-diaminedichloro-platinum$^{(II)}$ (DDP). In these complexes, two relatively inert ligands, such as amine, sulfur or nitrogen containing compounds, or other electron donating groups linked to a reporter, act as stabilizers while the other two groups are labile (e.g., chloride ions). Platinum complexes such as these have a marked affinity for the $N^{7}$-nitrogen atom in the purine nucleotide bases guanine and adenine in nucleic acids (FIG. 2). Upon reaction with nucleic acids, the labile chlorine atoms are displaced and Pt carrying the marker group, forms a non-covalent but irreversible adduct with the nucleotide bases, particularly guanine and adenine. The resulting adduct does not interfere with hybridization of DNA to its complementary target. Studies have shown that cis-DDP mainly forms intrastrand cross links to adjacent bases GG (47–50%) and AG (23–28%), and that less than 10% of cis-DDP formed intrastrand cross-links with adjacent guanines on the opposite strand of double stranded DNA (Fichtinger-Schlepman et al., 1985, Biochemistry 24: 707). cis-Platinum complexes with a single leaving group can also link to nucleic acid bases at individual G and A residues to form adducts (FIG. 3). Because platinum complexes are water soluble and chemically stable, no precipitation occurs at neutral pH, as can happen with other transition metal complexes.

cis-Platinum labeling compounds are disclosed in U.S. Pat. Nos. 5,985,566, 5,580,990, 5,714,327, 4,843,161, 4,569,932 and 4,207,416, International Patent Applications WO 92/01699, WO 96/35696, WO98/15564 and EP 0539466B1. A number of other cis-platinum compounds are known in the art for their activity as inhibitors of DNA synthesis, making them useful as chemotherapeutic agents.

The novel cis-platinum labeling compounds disclosed herein are useful for the direct, rapid, simple and highly efficient labeling of nucleic acids for hybridization assays, including single- or double-stranded DNA, RNA, PNA, oligonucleotides, and homoduplexes, heteroduplexes and multiplexes thereof. The novel compounds disclosed herein are also useful for the rapid, high efficiency labeling of any biomolecule of interest that has an available nitrogen or sulfur group, including, for example, nucleotides and nucleosides, amino acids, peptides, polypeptides, proteins, enzymes, glycoproteins, lipoproteins and other peptide based biomolecules, whether naturally occurring or synthetic, carbohydrates and lipids.

SUMMARY OF THE INVENTION

The invention provides novel platinum-based labeling compounds which, upon reaction with biomolecules serve to irreversibly attach detectable markers to those biomolecules. The platinum-based labeling compounds attach to the target biomolecules via coordination of the platinum (II) metal center with nitrogen or sulfur atoms on the target biomolecule.

The invention further encompasses a method for making platinum-based labeling compounds.

The invention further encompasses nucleic acid probe molecules labeled with the disclosed novel platinum-based labeling compounds and methods for making such labeled probe molecules.

The invention further encompasses methods of using probes labeled with platinum-based labeling compounds according to the invention. While any method calling for a labeled probe can make use of probes labeled with platinum-based labeling compounds according to the invention, preferred methods include array and microarray hybridization assays.

Further, the invention encompasses kits for labeling biomolecules using the novel platinum-based labeling compounds disclosed herein.

The invention encompasses a composition comprising the formula:

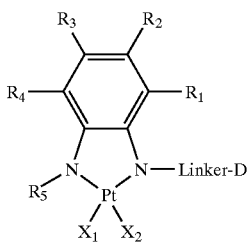

wherein:

$R_1$–$R_5$ may be the same or different and are independently selected from the group consisting of H, alkyl (1 to 10 carbon atoms), benzyl, sulfonate, phosphonate, $NO_2$, $CF_3$, halogen, O—$R_6$, —(C=O)$OR_6$, or —$OCH_2$(C=O)$R_6$ and a salt, wherein $R_6$ is a straight or branched, saturated or unsaturated, substituted or unsubstituted alkyl having 1–10 carbons;

$X_1$ and $X_2$ may be the same or different and X is a leaving group; and linker is a moiety joining a nitrogen to a detectable marker, D.

In one embodiment, the leaving group is selected from the group consisting of $NO_3$, halogen CN, $OCOR_7$, OCO-Phenyl, $OCOCH_2OC(Phenyl)_3$, O-Trityl and 3,5-demethyl-phenyl-4-sulfate, wherein $R_7$ is selected from the group consisting of H, methyl, benzyl, sulfonate, phosphonate, $NO_2$, $CF_3$, halogen, O—$R_6$, —(C=O)$OR_6$, —$OCH_2$(C=O)$R_6$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

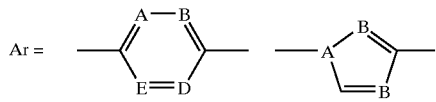

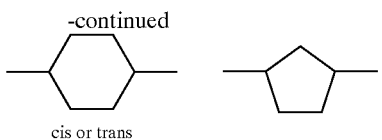

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

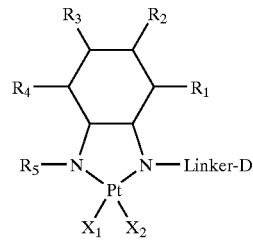

wherein:

$R_1$–$R_5$ may be the same or different and are independently selected from the group consisting of H, methyl, benzyl, sulfonate, phosphonate, $NO_2$, $CF_3$, halogen, O—$R_6$, —(C=O)$OR_6$, or —$OCH_2$(C=O)$R_6$ and a salt, wherein $R_6$ is a straight or branched, saturated or unsaturated, substituted or unsubstituted alkyl having 1–10 carbons;

$X_1$ and $X_2$ may be the same or different and X is a leaving group; and linker is a moiety joining a nitrogen to a detectable marker, D.

In one embodiment, the leaving group is selected from the group consisting of $NO_3$, halogen, CN, $OCOR_7$, OCO-Phenyl, $OCOCH_2OC(Phenyl)_3$, O-Trityl and 3,5-dimethyl-phenyl-4-sulfate, wherein $R_7$ is selected from the group consisting of H, methyl, benzyl, sulfonate, phosphonate, $NO_2$, $CF_3$, halogen, O—$R_6$, —(C=O)$OR_6$, —$OCH_2$(C=O)$R_6$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

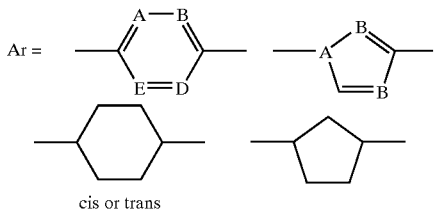

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

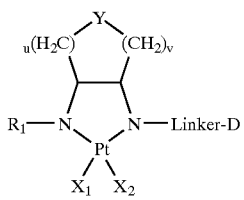

wherein

Y is selected from the group consisting of O, S, and C;
$R_1$ is selected from the group consisting of H, methyl, benzyl, sulfonate, phosphonate, $NO_2$, $CF_3$, halogen, O—$R_2$, —(C=O)O$R_2$, —OCH$_2$(C=O)$R_2$, and a salt, wherein $R_2$ is a straight or branched, saturated or unsaturated, substituted or unsubstituted alkyl having 1–10 carbons;
$X_1$ and $X_2$ are the same or different and X is a leaving group;
linker is a moiety joining a nitrogen to a detectable marker, D, and u and v are the same or different and are an integer from 1 to 10.

In one embodiment, the leaving group is selected from the group consisting of $NO_3$, halogen, CN, OCOR$_3$, OCO-Phenyl, OCOCH$_2$OC(Phenyl)$_3$, O-Trityl and 3,5-dimethyl-phenyl-4-sulfate, wherein $R_3$ is selected from the group consisting of H, methyl, benzyl, sulfonate, phosphonate, $NO_2$, $CF_3$, halogen, O—$R_2$, —(C=O)O$R_2$, or —OCH$_2$(C=O)$R_2$ and a salt. In another embodiment, the linker is selected from the group consisting of: (CH$_2$)n, (CH$_2$)$_n$(CH=CH)$_m$O(CH=CH)$^p$(CH$_2$)$_q$, CO(CH$_2$)$_n$(CH=CH)$_m$ (CH$_2$)$_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

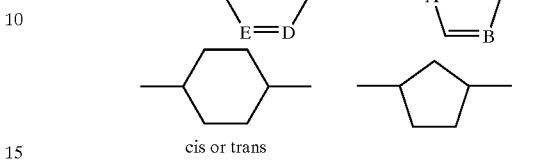

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

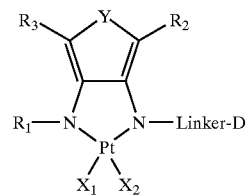

wherein:

—Y is selected from the group consisting of O, S, and C;
$R_1$–$R_3$ may be the same or different and are independently selected from the group consisting of H, methyl, benzyl, sulfonate, phosphonate, $NO_2$, $CF_3$, halogen, O—$R_4$, —(C=O)O$R_4$, or —OCH$_2$(C=O)$R_4$ and a salt, wherein $R_4$ is a straight or branched, saturated or unsaturated, substituted or unsubstituted alkyl having 1–10 carbons;
$X_1$ and $X_2$ are the same or different and X is a leaving group; and
linker is a moiety joining a nitrogen to a detectable marker, D.

In one embodiment, the leaving group is selected from the group consisting of $NO_3$, halogen, CN, OCOR$_5$, OCO-Phenyl, OCOCH$_2$OC(Phenyl)$_3$, O-Trityl and 3,5-dimethyl-phenyl-4-sulfate, wherein $R_5$ is selected from the group consisting of H, methyl, benzyl, sulfonate, phosphonate, NO$_2$, CF$_3$, halogen, O—R$_4$, —(C=O)OR$_4$, —OCH$_2$(C=O)R$_4$ and a salt.

In another embodiment, the linker is selected from the group consisting of: (CH$_2$)n, (CH$_2$)$_n$(CH=CH)$_m$O(CH=CH)$_p$(CH$_2$)$_q$, CO(CH$_2$)$_n$(CH=CH)$_m$(CH$_2$)$_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

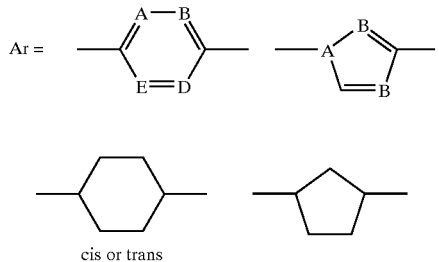

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

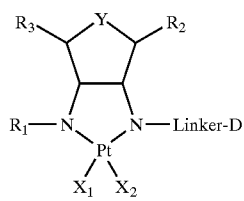

wherein:

Y is selected from the group consisting of O, S, and C;

R$_1$–R$_3$ may be the same or different and are independently selected from the group consisting of H, methyl, benzyl, sulfonate, phosphonate, NO$_2$, CF$_3$, halogen, O—R$_4$, —(C=O)OR$_4$, or —OCH$_2$(C=O)R$_4$ and a salt, wherein R$_4$ is a straight or branched, saturated or unsaturated, substituted or unsubstituted alkyl having 1–10 carbons;

X$_1$ and X$_2$ are the same or different and X is a leaving group; and linker is a moiety joining a nitrogen to a detectable marker, D.

In one embodiment, the leaving group is selected from the group consisting of No$_3$ halogen, CN, OCOR$_5$, OCO-Phenyl, OCOCH$_2$OC(Phenyl)$_3$, O-Trityl and 3,5-dimethyl-phenyl-4-sulfate, wherein R$_5$ is selected from the group consisting of H, methyl, benzyl, sulfonate, phosphonate, NO$_2$, CF$_3$, halogen, O—R$_4$, —(C=O)OR$_4$, —OCH$_2$(C=O)R$_4$ and a salt.

In another embodiment, the linker is selected from the group consisting of: (CH$_2$)n, (CH$_2$)$_n$(CH=CH)$_m$O(CH=CH)$_p$(CH$_2$)$_q$, CO(CH$_2$)$_n$(CH=CH)$_m$(CH$_2$)$_p$, COAr(CH$_2$)n(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

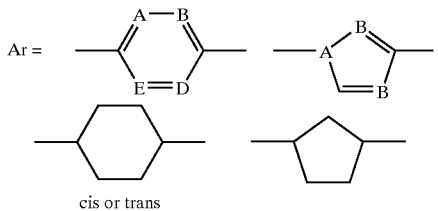

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula

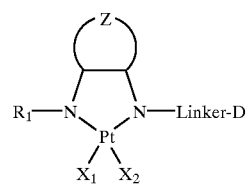

wherein

Z is selected from the group consisting of (CH$_2$)n, and (CH$_2$)nO(CH$_2$)m, wherein m and n are integers from 2 to 8, inclusive;

R$_1$ is selected from the group consisting of H, methyl, benzyl, sulfonate, phosphonate, NO$_2$, CF$_3$, halogen, O—R$_2$, —(C=O)OR$_2$, or —OCH$_2$(C=O)R$_2$ and a salt, wherein R$_2$ is a straight or branched, saturated or unsaturated, substituted or unsubstituted alkyl having 1–10 carbons;

$X_1$ and $X_2$ are the same or different and X is a leaving group; and linker is a moiety joining a nitrogen to a detectable marker, D.

In one embodiment, the leaving group is selected from the group consisting of $NO_3$, halogen, CN, $OCOR_3$, OCO-Phenyl, $OCOCH_2OC(Phenyl)_3$, O-Trityl and 3,5-dimethyl-phenyl-4-sulfate, wherein $R_3$ is selected from the group consisting of H, methyl, benzyl, sulfonate, phosphonate, $NO_2$, $CF_3$, halogen, $O-R_2$, $-(C=O)OR_2$, $-OCH_2(C=O)R_2$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, COAr $(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, $-S-S-$, NHCSNH, NHCSO, wherein

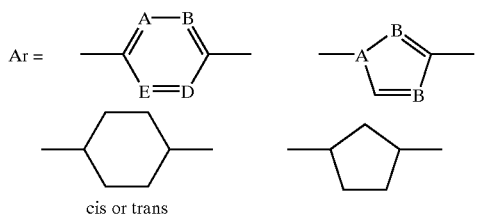

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula

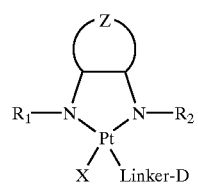

wherein

Z is selected from the group consisting of $(CH_2)_n$, and $(CH_2)_nO(CH_2)_m$, wherein m and n are integers from 2 to 8, inclusive;

$R_1$ and $R_2$ may be the same or different and are selected from the group consisting of H, methyl, benzyl, sulfonate, phosphonate, $NO_2$, $CF_3$, halogen, $O-R_3$, $-(C=O)OR_3$, or $-OCH_2(C=O)R_3$ and a salt, wherein $R_3$ is a straight or branched, saturated or unsaturated, substituted or unsubstituted alkyl having 1–10 carbons;

$X_1$ is a leaving group; and linker is a moiety joining a detectable marker, D to the platinum ion.

In one embodiment, the leaving group is selected from the group consisting of $NO_3$, halogen, CN, $OCOR_4$, OCO-Phenyl, $OCOCH_2OC(Phenyl)_3$, O-Trityl and 3,5-dimethyl-phenyl-4-sulfate, wherein $R_4$ is selected from the group consisting of H, methyl, benzyl, sulfonate, phosphonate, $NO_2$, $CF_3$, halogen, $O-R_3$, $-(C=O)OR_3$, $-OCH_2(C=O)R_3$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, COAr $(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, $-S-S-$, NHCSNH, NHCSO, wherein

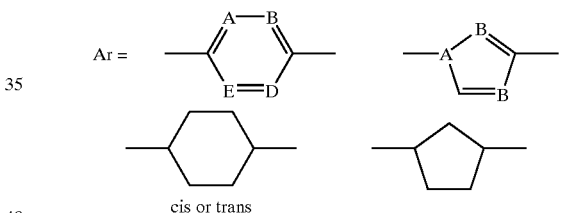

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

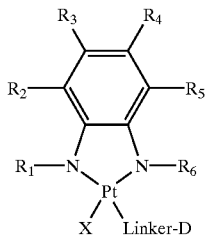

wherein:

$R_1$–$R_6$ may be the same or different and are independently selected from the group consisting of H, methyl, benzyl, sulfonate, phosphonate, $NO_2$, $CF_3$, halogen, O—$R_7$, —(C=O)O$R_7$, or —OCH$_2$(C=O)$R_7$ and a salt, wherein $R_7$ is a straight or branched, saturated or unsaturated, substituted or unsubstituted alkyl having 1–10 carbons;

X is a leaving group; and linker is a moiety joining a detectable marker, D to the platinum ion.

In one embodiment, the leaving group is selected from the group consisting of $NO_3$, halogen, CN, OCOR$_8$, OCO-Phenyl, OCOCH$_2$OC(Phenyl)$_3$, O-Trityl and 3,5-dimethyl-phenyl-4-sulfate, wherein $R_8$ is selected from the group consisting of H, methyl, benzyl, sulfonate, phosphonate, $NO_2$, $CF_3$, halogen, O—$R_7$, —(C=O)O$R_6$, —OCH$_2$(C=O)$R_7$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)m(CH_2)_p$, COAr$(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

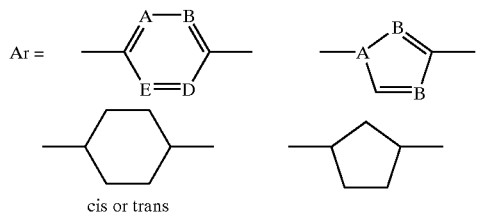

and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula

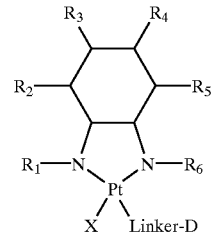

wherein $R_1$–$R_6$ may be the same or different and are independently selected from the group consisting of H, methyl, benzyl, sulfonate, phosphonate, $NO_2$, $CF_3$, halogen, O—$R_7$, —(C=O)O$R_7$, or —OCH$_2$(C=O)$R_7$ and a salt, wherein $R_7$ is a straight or branched, saturated or unsaturated, substituted or unsubstituted alkyl having 1–10 carbons;

X is a leaving group; and linker is a moiety joining a detectable marker, D, to the platinum ion.

In one embodiment, the leaving group is selected from the group consisting of $NO_3$, halogen, CN, OCOR$_8$, OCO-Phenyl, OCOCH$_2$OC(Phenyl)$_3$, O-Trityl and 3,5-dimethyl-phenyl-4-sulfate, wherein $R_8$ is selected from the group consisting of H, methyl, benzyl, sulfonate, phosphonate, $NO_2$, $CF_3$, halogen, O—$R_7$, —(C=O)O$R_6$, —OCH$_2$(C=O)$R_7$ and a salt.

In another embodiment, the linker is selected from the group consisting of: $(CH_2)n$, $(CH_2)_n(CH=CH)_mO(CH=CH)_p(CH_2)_q$, $CO(CH_2)n(CH=CH)_m(CH_2)_p$, COAr$(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a composition comprising the formula:

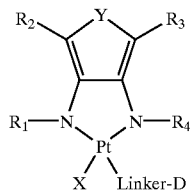

wherein

Y is selected from the group consisting of O, S, and C;
$R_1$–$R_4$ may be the same or different and are independently selected from the group consisting of H, methyl, benzyl, sulfonate, phosphonate, $NO_2$, $CF_3$, halogen, O—$R_5$, —(C=O)$OR_5$, or —$OCH_2$(C=O)$R_5$ and a salt, wherein $R_5$ is a straight or branched, saturated or unsaturated, substituted or unsubstituted alkyl having 1–10 carbons;
X is a leaving group; and
linker is a moiety joining a detectable marker, D, to the platinum ion.

In one embodiment, the leaving group is selected from the group consisting of $NO_3$, halogen, CN, $OCOR_6$, OCO-Phenyl, $OCOCH_2OC(Phenyl)_3$, O-Trityl and 3,5-dimethylphenyl-4-sulfate, wherein $R_6$ is selected from the group consisting of H, methyl, benzyl, sulfonate, phosphonate, $NO_2$, $CF_3$, halogen, O—$R_5$, —(C=O)$OR_5$, —$OCH_2$(C=O)$R_5$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

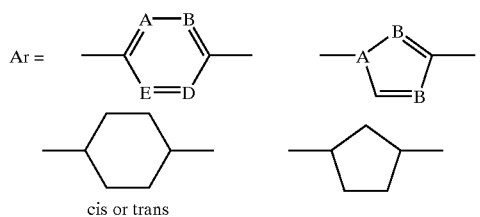

cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

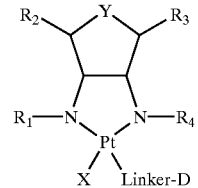

The invention further encompasses a composition comprising the formula:
wherein

Y is selected from the group consisting of O, S, and C;
$R_1$–$R_4$ may be the same or different and are independently selected from the group consisting of H, methyl, benzyl, sulfonate, phosphonate, $NO_2$, $CF_3$, halogen, O—$R_5$, —(C=O)$OR_5$, or —$OCH_2$(C=O)$R_5$ and a salt, wherein $R_5$ is a straight or branched, saturated or unsaturated, substituted or unsubstituted alkyl having 1–10 carbons;
X is a leaving group; and
linker is a moiety joining a detectable marker, D, to the platinum ion.

In one embodiment, the leaving group is selected from the group consisting of $NO_3$, halogen, CN, $OCOR_6$, OCO-Phenyl, $OCOCH_2OC(Phenyl)_3$, O-Trityl and 3,5-dimethylphenyl-4-sulfate, wherein $R_6$ is selected from the group consisting of H, methyl, benzyl, sulfonate, phosphonate, $NO_2$, $CF_3$, halogen, O—$R_5$, —(C=O)$OR_5$, —$OCH_2$(C=O)$R_5$ and a salt.

In another embodiment, the linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein cis or trans and A, B, D, and E are the same or different and are selected from the group consisting of CH, N, O and S.

In another embodiment, the detectable marker, D, is selected from the group consisting of a fluorophore, a chromophore, a radiolabel, an enzyme and an affinity tag.

The invention further encompasses a nucleic acid comprising a composition according to the formula above and the additional embodiments described above. In a preferred embodiment, the composition forms an adduct with the nucleic acid.

The invention further encompasses a probe comprising a nucleic acid comprising a composition according to the embodiments described above.

The invention further encompasses a method of labeling a nucleic acid, the method comprising the step of contacting a composition as described above with the nucleic acid.

The invention further encompasses a method of probing a nucleic acid array, the method comprising the steps of contacting the array with a probe as described and detecting signal from the detectable marker.

The invention further encompasses a method of making a platinum labeling compound that comprises a stabilizing bridge, the method comprising the step of contacting potassium tetrachloroplatinate (II) with an aliphatic diamine labeled with a detectable marker, wherein the contacting results in a cis-platinum dichloride labeling compound.

In one embodiment, the aliphatic diamine is a cycloaliphatic diamine.

In another embodiment, the cycloaliphatic diamine is a 1,2-cycloaliphatic diamine.

In another embodiment, the cycloaliphatic diamine is a cyclohexyl diamine.

In another embodiment, the cyclohexyl diamine is a 1,2-cyclohexyl diamine.

In another embodiment, the contacting is performed in aqueous solution at a pH of about 1.5 to 5.5 and at a temperature of about 65° C.

Definitions:

As used herein, the term "platinum labeling complex" or "platinum labeling compound" refers to a molecule that comprises a tetravalent platinum atom, a cycloaliphatic diamine stabilizing bridge, and a detectable marker, wherein the platinum atom has the ability to form an adduct with one or more biomolecules.

As used herein, the term "biomolecule" refers to a molecule found within or made by an organism in nature. The term biomolecule also refers to chemically modified or synthetic forms of molecules found within or made by an organism in nature. Biomolecules of interest include, but are not limited to, nucleic acids (oligonucleotides or polynucleotides of DNA, RNA or PNA), peptides, polypeptides, proteins, carbohydrates and lipids.

As used herein, the term "cycloaliphatic diamine" refers to substituted or unsubstituted aliphatic diamines comprising at least one cyclic structure.

As used herein, the term "adduct" refers to the complex formed by the co-ordination of the platinum atom in a platinum labeling complex to an atom of a biomolecule. In an adduct as used herein, the platinum atom directly participates in the binding of the platinum labeling complex to the biomolecule. The adducts formed by platinum labeling complexes are essentially irreversible.

As used herein, the term "detectable marker" refers to a moiety that, when attached to a biomolecule, confers detectability upon that biomolecule or another molecule to which the biomolecule binds. Fluorescent moieties are preferred detectable markers according to the invention, but detectable markers also include, for example, isotopes, fluorescent proteins and peptides, enzymes, components of a specific binding pair, chromophores, affinity tags as defined herein, antibodies, colloidal metals (i.e. gold) and quantum dots. Detectable markers may be either directly or indirectly detectable. Directly detectable markers do not require additional reagents or substrates in order to generate detectable signal. Examples include isotopes and fluorophores. Indirectly detectable markers require the presence or action of one or more co-factors or substrates. Examples include enzymes such as β-galactosidase which is detectable by generation of colored reaction products upon cleavage of substrates such as the chromogen X-gal (5-bromo-4-chloro-3-indoyl-β-D-galactopyranoside), horseradish peroxidase which is detectable by generation of a colored reaction product in the presence of the substrate diaminobenzidine and alkaline phosphatase which is detectable by generation of colored reaction product in the presence of nitroblue tetrazolium and 5-bromo-4-chloro-3-indolyl phosphate, and affinity tags.

As used herein, the term "leaving group" refers to a moiety that can be displaced from the platinum atom in a platinum labeling complex as described herein, in favor of a molecule to be labeled under appropriate conditions. The selection of leaving groups is within the ability of one skilled in the art, through comparison of the electronegativities of the target molecule and the candidate leaving group. That is, a relatively more electronegative group on the target molecule will tend to displace a relatively less electronegative leaving group. For example, suitable leaving groups for labeling a nucleic acid would include groups that would permit a bond between the platinum ion and the nucleic acid to be formed under appropriate conditions. Leaving groups include, for example, F, $NO_2$, Ots, $SOPO_4$, Cl, Br, I, CN, N3, NR3, OAr, OR, SR, $SO_2R$ and $NH_2$, where R is an organic residual group and Ar is an aryl organic residual group. Others include, for example, sulfate, nitrate, phosphate, carbonate and lower alkyl derivatives thereof (e.g., ethylnitrate, propylnitrate, etc.).

As used herein, "appropriate conditions" refers to solutions containing molecules having "soft" ligands such as heavier halogens, phosphines, sulfides, nitrogen compounds such as amines, adenine, adenosine and its derivatives, guanine, guanosine and its derivatives, DNA, RNA, PNA, alkenes, alkynes and other π-compounds, heated to 15–100° C. between 0.5 to 120 minutes.

As used herein, the term "fluorophore" refers to a detectable moiety that, upon absorbing light energy of a given wavelength (the "excitation wavelength"), is excited and emits light of a longer wavelength (the emission wavelength).

As used herein, the term "chromophore" refers to a chemical group capable of selective light absorption resulting in the coloration of compounds or entities containing it.

As used herein, the term "affinity tag" refers to a moiety that is selectively bound by an affinity reagent. The attachment of an affinity tag to a biomolecule confers upon the biomolecule the ability to be selectively bound by the affinity reagent. As used herein, the term "affinity reagent" refers to an agent that selectively binds to an affinity tag. Useful affinity tag pairs include, for example, antibody and antigen, and biotin and avidin or streptavidin. A pair of molecules exhibits "selective binding" if they physically bind one another in the presence of other different molecules to the substantial exclusion of such different molecules. As used herein, the term "polynucleotide" refers to a polymer of two or more nucleotide monomers or analogs thereof, and includes double- or single-stranded DNA, RNA or PNA (peptide nucleic acid). A "polynucleotide" may comprise modified nucleotides, the modification lying in the backbone sugar moiety, the linkage between nucleotides or in the nucleoside base. For example, the sugar moiety can be a ribose, deoxyribose, dideoxyribose, or a modified form of any of these. The phosphate linkage between nucleotides can be modified as, for example, a phosphorothioate-, methylphosphonate- or phosphoramidate linkage, or the nucleobases can be linked by pseudopeptide linkages in place of sugar-phosphate diester linkages, as in PNAs. The nucleoside base can be, for example, a purine, deazapurine or pyrimidine, for example adenine, guanine, cytosine, thymine, uracil, inosine, deaazaadenine, deazaguanosine, and the like. Non-limiting examples of nucleobase analogs that may be incorporated into a "polynucleotide" as the term is used herein include hypoxanthine, pseudouridine, isocytosine, isoguanine, and 2-thiopyrimidine.

As used herein, the term "oligonucleotide" refers to a polynucleotide that is between two and about 200 nucleotides in length. An oligonucleotide can be a synthetic (i.e., chemically synthesized) molecule, an enzymatically synthesized molecule or a naturally occurring molecule.

As used herein, the term "probe" refers to a biomolecule that specifically binds a target biomolecule or class of target biomolecules. Biomolecules useful as probes are preferably oligonucleotides or polynucleotides, but may include, for example, peptides (including peptide antigens), polypeptides (including, but not limited to antibodies, antigen-binding fragments thereof, and polypeptide antigens), carbohydrates, lipids, hormones and neurotransmitters. As used herein, a "probe" is either directly or indirectly detectable.

As used herein, a "nucleic acid probe" is a polynucleotide of at least 10 nucleotides (nt), 15 nt, 20 nt, 30 nt, 40 nt, 50 nt, 75 nt, 100 nt, 200 nt, 500 nt, 1000 nt, and even up to 5000 to 10,000 nt in length.

As used herein, the term "array" refers to a plurality of biomolecule samples immobilized in distinct locations on a substrate. A nucleic acid array is an array of nucleic acid samples, each sample comprising DNA, RNA, PNA or a polypeptide or protein mixture thereof. A polypeptide or protein array is an array of peptide samples, each sample comprising peptides, oligopeptides, polypeptides, proteins or a mixture thereof As used herein, the term "linker" refers to a chemical moiety that joins a detectable marker, as defined herein, to a platinum labeling complex according to the invention. The linker can be attached either to a terminal nitrogen of the cycloaliphatic diamine bridge, or it can be coordinated to one of the two platinum coordination sites that does not participate in the bridge structure.

DETAILED DESCRIPTION OF THE INVENTION

Figure 1:
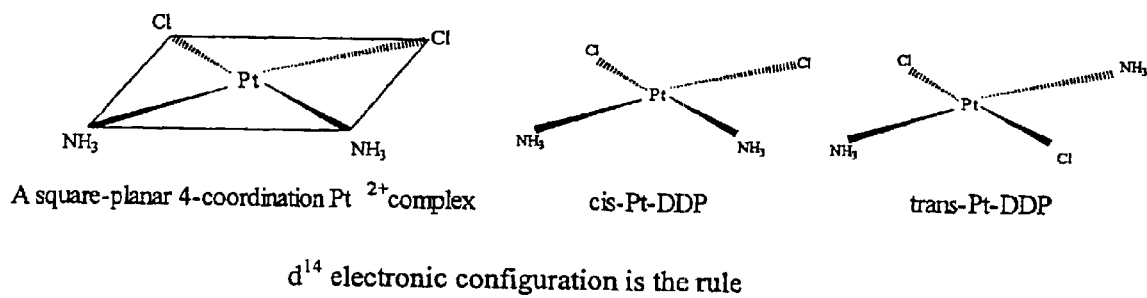
FIG. 1 shows the structures of cis- and trans-diaminedichloroplatinum (II). The cis version is referred to as cis-DDP.
Figure 2:
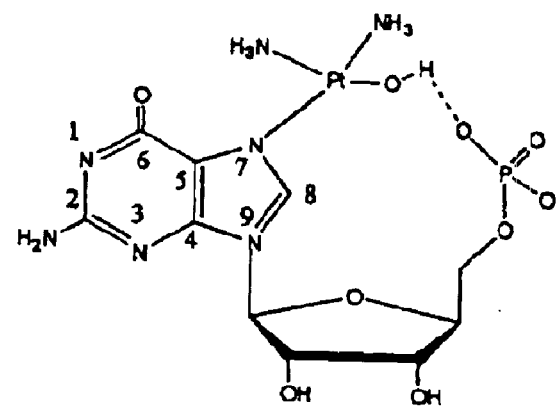
FIG. 2 shows the coordination of the Pt(II) ion with $N^7$ of a guanine DNA base.
Figure 3:
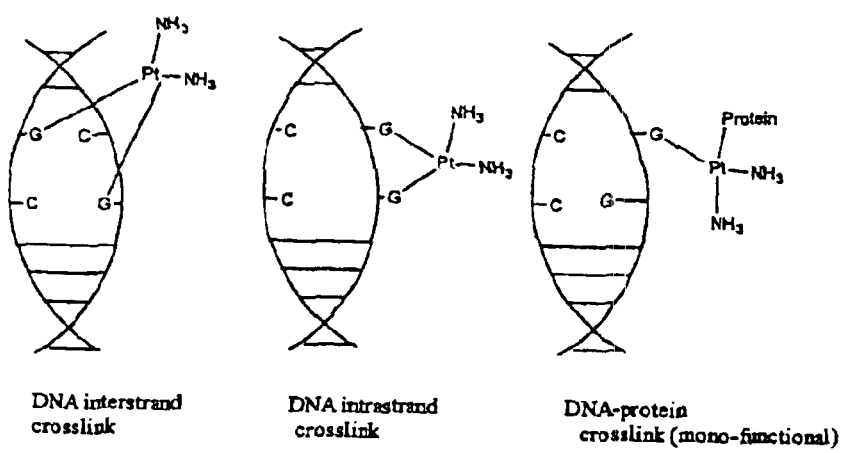
FIG. 3 shows cis-Pt adduct formation with DNA, forming interstrand cross-links (bifunctional Pt compound), intrastrand cross-links (bifunctional Pt compound) and a DNA-protein cross-link (monofunctional Pt compound).

The invention provides novel platinum-based compounds for detectably labeling biomolecules, as well as methods using such compounds appropriate for research and diagnostic medical uses. The compounds and methods disclosed permit the highly efficient, rapid and simple labeling of biomolecules including, but not limited to nucleic acids (single and double-stranded DNA, RNA, PNA, and combinations thereof, including synthetic or naturally-occurring homoduplexes, heteroduplexes, oligonucleotides and polynucleotides), nucleotides, nucleosides and derivatives thereof, amino acids, peptides, polypeptides, proteins, enzymes, glycoproteins, lipoproteins, carbohydrates and lipids.

The compounds disclosed are well suited for the detectable labeling of nucleic acid probes for hybridization assays. Platinum-based labeling compounds may be used to label nucleic acids by reaction of the compounds with nucleotide or nucleoside precursors to generate labeled nucleotide or nucleoside precursors, followed by enzymatic incorporation of labeled nucleotide into a probe molecule. A preferred approach, however, completely avoids the use of enzymes and generates high specific activity labeled probes much more rapidly than methods requiring enzymes. In this approach, the platinum compounds bearing detectable markers are directly reacted with the nucleic acid probe molecules, resulting in non-covalent, but essentially irreversible adduct formation with the probe. After simple ethanol precipitation or size exclusion column chromatography, the probe labeled in this manner is ready to use in any hybridization assay compatible with the detectable marker used.

The disclosure provided aims to permit one of skill in the art to make the novel platinum-based labeling compounds disclosed, including the generation of the cis-platinum complex itself and the attachment of a detectable marker to the platinum complex, as well as how to react the platinum compound with a biomolecule, purify the labeled biomolecule probe away from the reactants, and use the labeled biomolecule probe in an assay.

I. cis-Platinum Labeling Compounds According to the Invention.

In one embodiment, a platinum-based labeling compound of the invention comprises the structure of Formula 1.

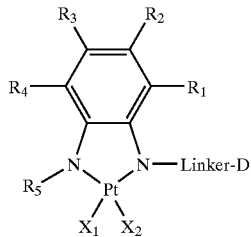

Formula 1 wherein $R_1$–$R_5$ may be the same or different and are independently selected from the group consisting of H, alkyl (1 to 10 carbon atoms), benzyl, sulfonate, phosphonate, $NO_2$, $CF_3$, halogen, O—$R_6$, —(C=O)O$R_6$, or —OCH$_2$(C=O)$R_6$ and a salt. $R_6$ is a straight or branched, saturated or unsaturated, substituted or unsubstituted alkyl having 1–10 carbons.

In the compound of Formula 1, $X_1$ and $X_2$ may be the same or different, and at least one of $X_1$ or $X_2$ is a leaving group. Leaving groups can be any group satisfying the definition of the term "leaving group" as it is defined herein. However, preferred leaving groups are selected from the group consisting of CN, OCOR$_7$, OCO-Phenyl, OCOCH$_2$OC(Phenyl)$_3$, O-Trityl, or 3,5-dimethyl-phenyl-4-sulfate

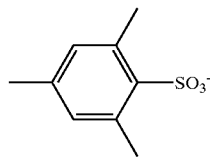

wherein $R_7$ is selected from the group consisting of H, methyl, benzyl, sulfonate, phosphonate, $NO_2$, $CF_3$, halogen, O—$R_6$, —(C=O)O$R_6$, —OCH$_2$(C=O)$R_6$ and a salt.

In Formula 1, "linker" is a chemical moiety that joins a nitrogen that is complexed with the platinum ion with a detectable marker, D. The linker in Formula 1 can be any group known in the art that satisfies the definition of the term "linker" as it is defined herein. Preferred linkers include those selected from the group consisting of: $(CH_2)n$, $CO(CH_2)_n(CH=CH)_m(CH_2)_p$, $(CH_2)_n(CH=CH)_mO$ $(CH=CH)_p(CH_2)_q$, $COAr(CH_2)_n(CH=CH)_m(CH_2)_p$, $NH_2$ $(CH_2)_nQ$, $NH_2((CH_2)_nO)_m(CH_2)_tQ$, $NH_2(CH_2)_mAr(CH_2)$ $_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

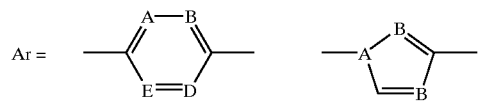

cis or trans and A, B, D, and E are the same or different and are selected from the group consisting of CH, N, O and S.

In the compound of Formula 1, the detectable marker, D, can be any molecule known in the art that is detectable, either directly or indirectly. Directly detectable markers useful with any of the platinum labeling compounds disclosed herein include those which are detectable without a requirement for additional co-factors or substrates, for example, radioisotopes (e.g., $^{32}P$, $^{33}P$, $^{35}S$, $^{125}I$, among others) and fluorophores. Preferred directly detectable markers include fluorophores, radioisotopes, colloidal dye substances, chromophores, particulate sols, colored latex sols and metal sols and colloidal metals/alloys such as quantum dots. More preferred are fluorophores, including but not limited to cyanine dyes, fluoresceins, rhodamines, eosins, trisulfonylpyrenes, infra-red dyes, green fluorescent proteins (GFP) and chemiluminescent molecules. Specific examples of dyes useful according to the invention include, but are not limited to, fluorescein and derivatives, rhodamine (TRITC) and derivatives, Hoechst 33258, phycobiliproteins such as R-Phycoerythrin (PE), Quantum Red™, Texas Red, Oregon Green, TAMRA, BODIPY, R6G, R110, ROX, Cy3, and Cy5, infra-red and near infra-red dyes and their derivatives, and porphyrins and their derivatives.

Indirectly detectable markers useful with any of the platinum labeling compounds disclosed herein include those which require a co-factor or substrate for detection. Examples include, but are not limited to, enzymes, such as β-galactosidase and alkaline phosphatase, that generate colored and/or fluorescent reaction products in the presence of appropriate chromogenic or fluorogenic substrates, a member of a specific binding pair, reducing substances, biotin, avidin, streptavidin, digoxigenin, dansyl lysine, antibodies and other affinity reagents or affinity tags (e.g., protein A, protein G, etc.). Preferred indirectly detectable markers include enzymes, affinity reagents and members of a specific binding pair.

In another embodiment, the platinum-based compound of the invention comprises the structure of Formula 2:

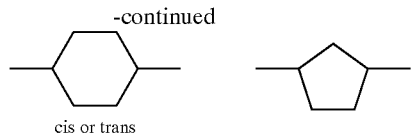

Formula 2

In the structure of Formula 2, $R_1$–$R_5$ may be the same or different and are independently selected from the group consisting of H, alkyl (1 to 10 carbon atoms), benzyl, sulfonate, phosphonate, $NO_2$, $CF_3$, halogen, O—$R_6$, —(C=O)O$R_6$, or —OCH$_2$(C=O)$R_6$ and a salt. $R_6$ is a straight or branched, saturated or unsaturated, substituted or unsubstituted alkyl having 1–10 carbons. Further, $X_1$ and $X_2$ may be the same or different, and at least one of $X_1$ and $X_2$ is a leaving group. The leaving groups specified in the

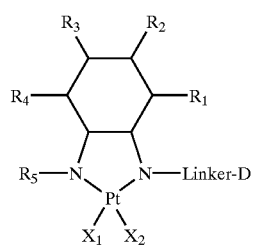

Ar = structure of Formula 2 and all subsequent structures specifying leaving groups have the same properties and preferences as those described for the leaving group of Formula 1.

The "Linker" in Formula 2, and in all subsequent formulae specifying a linker, has the same properties and preferences as those of the linker of Formula 1. Similarly, the detectable marker, D, specified in Formula 2 and in all subsequent formulae specifying a detectable marker, has the same properties and preferences as those of the detectable marker, D, of Formula 1.

In another embodiment, the platinum-based labeling compound of the invention comprises the structure of Formula 3:

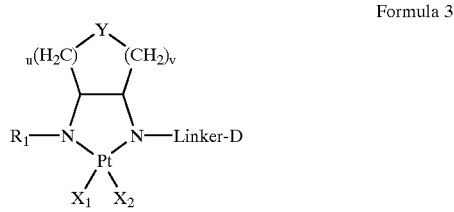

Formula 3

In the structure of Formula 3, Y is selected from the group consisting of O, S, and C, and $R_1$ is selected from the group consisting of H, methyl, benzyl, sulfonate, phosphonate, $NO_2$, $CF_3$, halogen, O—$R_2$, —(C=O)O$R_2$, —OCH$_2$(C=O)$R_2$, and a salt, wherein $R_2$ is a straight or branched, saturated or unsaturated, substituted or unsubstituted alkyl having 1–10 carbons. $X_1$ and $X_2$ in Formula 3 are the same or different and at least one of $X_1$ and $X_2$ is a leaving group as described for Formula 1. The "Linker" and detectable marker, D, are as described for Formula 1, and u and v are the same or different and are an integer from 1 to 10.

In another embodiment, the platinum-based compound of the invention comprises the structure of Formula 4:

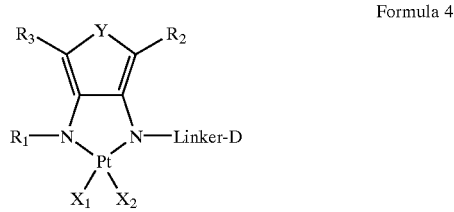

Formula 4

In the structure of Formula 4, Y is selected from the group consisting of O, S, and C. $R_1$–$R_3$ may be the same or different and are independently selected from the group consisting of H, methyl, benzyl, sulfonate, phosphonate, $NO_2$, $CF_3$, halogen, O—$R_4$, —(C=O)O$R_4$, or —OCH$_2$(C=O)$R_4$ and a salt, wherein $R_4$ is a straight or branched, saturated or unsaturated, substituted or unsubstituted alkyl having 1–10 carbons. $X_1$ and $X_2$ are the same or different and at least one of $X_1$ and $X_2$ is a leaving group with the properties and preferences of leaving groups described for Formula 1. The "Linker" and detectable marker, "D", of Formula 4 are as described for Formula 1.

In another embodiment, the platinum-based labeling compound of the invention comprises the structure of Formula 5:

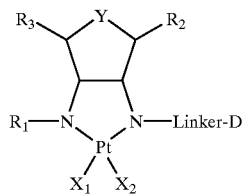

Formula 5

In the structure of Formula 5, Y is selected from the group consisting of O, S, and C. $R_1$–$R_3$ may be the same or different and are independently selected from the group consisting of H, methyl, benzyl, sulfonate, phosphonate, $NO_2$, $CF_3$, halogen, O—$R_4$, —(C=O)O$R_4$, or —OCH$_2$(C=O)$R_4$ and a salt, wherein $R_4$ is a straight or branched, saturated or unsaturated, substituted or unsubstituted alkyl having 1–10 carbons. $X_1$ and $X_2$ are the same or different, and at least one of $X_1$ and $X_2$ is a leaving group with the properties and preferences of leaving groups described for Formula 1. The "Linker" and detectable marker, "D", of Formula 5 have the same properties and preferences as those for Formula 1.

In another embodiment, the platinum-based labeling compound of the invention comprises the structure of Formula 6:

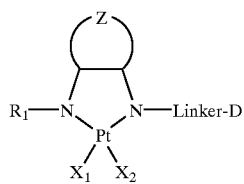

Formula 6

In the structure of Formula 6, Z is selected from the group consisting of $(CH_2)_n$, and $(CH_2)_nO(CH_2)_m$, wherein m and n are integers from 2 to 8, inclusive. $R_1$ is selected from the group consisting of H, methyl, benzyl, sulfonate, phosphonate, $NO_2$, $CF_3$, halogen, O—$R_2$, —(C=O)O$R_2$, or —OCH$_2$(C=O)$R_2$ and a salt, wherein $R_2$ is a straight or branched, saturated or unsaturated, substituted or unsubstituted alkyl having 1–10 carbons. $X_1$ and $X_2$ are the same or different, and at least one of $X_1$ and $X_2$ is a leaving group with the properties and preferences of leaving groups described for Formula 1. The "Linker" and detectable marker, "D", of Formula 6 have the same properties and preferences as those for Formula 1.

In the structures of formulae 1–6, when only one of $X_1$ and $X_2$ is a leaving group, the other is a blocking group or another detectable marker. Non-limiting examples include fluorescein isothiocyanate (FITC) or other fluorophore, ethyl amine, DMSO, and thio-compounds such as SR, where R is an alkyl group.

Apart from the cyclic structure comprised by the stabilizing bridge present on all platinum-based labeling structures according to the invention, a distinction of the compounds of Formulae 1–6 over the prior art is that the structures have each of a stabilizing bridge structure, a detectable marker, and the potential for two leaving groups. Prior art structures with a stabilizing bridge structure have attached the detectable marker to the platinum atom through a linker, thereby occupying one of the co-ordination sites on the metal atom and thus reducing to one the number of sites available for a leaving group. Compounds of Formulae 1–6 attach the detectable marker through a linker attached to one of the stabilizing bridge nitrogens, which maintains two co-ordination sites available for adduct formation. The presence of two leaving groups preserves the possibility of using the labeling compounds as cross-linking reagents to increase the stability of the cross-linked pairs, such as hybridized nucleic acids. The presence of two leaving groups also permits cross-linking of a labeled biomolecule to a solid substrate or other molecule, where desired. It is also beneficial in some circumstances that, when there are two leaving groups, the two leaving groups are different from each other. This provides the possibility of exploiting differential displacement of the leaving groups in order to attach the platinum compound to two different moieties. It is specifically noted that platinum labeling compounds according to any of Formulae 1–6 herein can also be monofunctional, bearing only one leaving group.

In compounds according to the invention, the ring structure forming a bridge between the two nitrogen atoms increases the stability of the Pt II metal center, especially when the Pt II metal center is coupled to nucleic acids (Cotton et al., in *Advanced Inorganic Chemistry*, 6th ed., John Wiley & Sons, Inc., N.Y. pg. 1071).

In another embodiment, the platinum-based labeling compound of the invention comprises the structure of Formula 7:

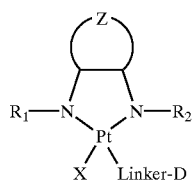

Formula 7

In the structure of Formula 7, Z is selected from the group consisting of $(CH_2)_n$, and $(CH_2)_nO(CH_2)_m$, wherein m and n are integers from 2 to 8, inclusive. $R_1$ and $R_2$ may be the same or different and are selected from the group consisting of H, alkyl (1 to 10 carbon atoms), benzyl, ulfonate, phosphonate, $NO_2$, $CF_3$, halogen, $O-R_3$, $-(C=O)OR_3$, or $-OCH_2(C=O)R_3$ and a salt, wherein $R_3$ is a straight or branched, saturated or unsaturated, substituted or unsubstituted alkyl having 1–10 carbons. $X_1$ is a leaving group with the properties and preferences of leaving groups described for Formula 1. The "Linker" and detectable marker, "D", of Formula 7 have the same properties and preferences as those for Formula 1.

In another embodiment, the platinum-based labeling compound of the invention comprises the structure of Formula 8:

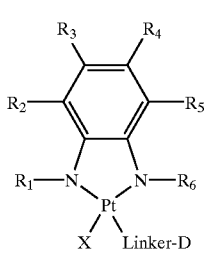

Formula 8

In the structure of Formula 8, $R_1$–$R_6$ may be the same or different and are independently selected from the group consisting of H, alkyl (1 to 10 carbon atoms), benzyl, sulfonate, phosphonate, $NO_2$, $CF_3$, halogen, $O-R_7$, $-(C=O)OR_7$, or $-OCH_2(C=O)R_7$ and a salt, wherein $R_7$ is a straight or branched, saturated or unsaturated, substituted or unsubstituted alkyl having 1–10 carbons. X is a leaving group with the properties and preferences of leaving groups described for Formula 1. The "Linker" and detectable marker, "D", of Formula 8 have the same properties and preferences as those for Formula 1.

In another embodiment, the platinum-based labeling compound of the invention comprises the structure of Formula 9:

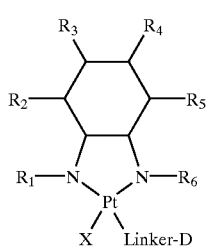

Formula 9

In the structure of Formula 9, $R_1$–$R_6$ may be the same or different and are independently selected from the group consisting of H, alkyl (1 to 10 carbon atoms), benzyl, sulfonate, phosphonate, $NO_2$, $CF_3$, halogen, $O-R_7$, $-(C=O)OR_7$, or $-OCH_2(C=O)R_7$ and a salt, wherein $R_7$ is a straight or branched, saturated or unsaturated, substituted or unsubstituted alkyl having 1–10 carbons. X is a leaving group with the properties and preferences of leaving groups described for Formula 1. The "Linker" and detectable marker, "D", of Formula 9 have the same properties and preferences as those for Formula 1.

In another embodiment, the platinum-based labeling compound of the invention comprises the structure of Formula 10:

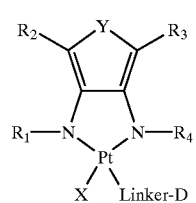

Formula 10

In the structure of Formula 10, Y is selected from the group consisting of O, S, and C. $R_1$–$R_4$ may be the same or different and are independently selected from the group consisting of H, alkyl (1 to 10 carbon atoms), benzyl, sulfonate, phosphonate, $NO_2$, $CF_3$, halogen, $O-R_5$, $-(C=O)OR_5$, or $-OCH_2(C=O)R_5$ and a salt, wherein $R_5$ is a straight or branched, saturated or unsaturated, substituted or unsubstituted alkyl having 1–10 carbons. X is a leaving group with the properties and preferences of leaving groups described for Formula 1. The "Linker" and detectable marker, "D", of Formula 10 have the same properties and preferences as those for Formula 1.

In another embodiment, the platinum-based labeling compound of the invention comprises the structure of Formula 11:

Formula 11

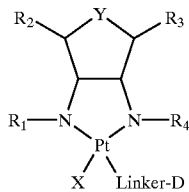

In the structure of Formula 11, Y is selected from the group consisting of O, S, and C. $R_1$–$R_4$ may be the same or different and are independently selected from the group consisting of H, alkyl (1 to 10 carbon atoms), benzyl, sulfonate, phosphonate, $NO_2$, $CF_3$, halogen, O—$R_5$, —(C=O)O$R_5$, or —OCH$_2$(C=O)$R_5$ and a salt, wherein $R_5$ is a straight or branched, saturated or unsaturated, substituted or unsubstituted alkyl having 1–10 carbons. X is a leaving group with the properties and preferences of leaving groups described for Formula 1. The "Linker" and detectable marker, "D", of Formula 11 have the same properties and preferences as those for Formula 1.

In another embodiment, a platinum-based labeling compound having a structure according to any one of Formulae 1–11 is reacted with a nucleic acid such that a leaving group, X, is displaced by a nitrogen on a purine nucleotide base and the platinum-based labeling compound forms a non-covalent adduct with the nucleic acid. The reaction of the nucleic acid and the platinum-based labeling compound generates a labeled nucleic acid useful as a detectable probe in nucleic acid hybridization reactions.

In another embodiment, a platinum-based labeling compound having a structure according to any one of Formulae 1–11 is reacted with a polypeptide such that a leaving group, X, is displaced by a sulfur or nitrogen on the polypeptide and the platinum-based labeling compound forms a non-covalent adduct with the polypeptide. The reaction of the polypeptide and the platinum-based labeling compound generates a labeled polypeptide useful as a detectable probe in quantitative and qualitative assays. Proteins with natural or engineered (by site-directed mutagenesis) amino groups (i.e., lysine residues), or sulflhydryl groups (i.e., cysteine) are candidate sites for attachment of the Cis-platinum labeling reagent.

II. Linkers Useful According to the Invention.

Linkers useful according to the invention serve to attach a detectable marker to the platinum compound that is responsible for binding to the target biomolecule. Linkers useful according to the invention can be simple alkyl chains or more complex structures comprising aryl groups and/or heteroatoms. One property any linker useful according to the invention must have is the ability to be joined to a reactive group suitable for the attachment of the detectable marker. Non-limiting examples of reactive groups include amines, carboxylate, and thiol groups. Linkers bearing amines are most preferred, and will frequently be reacted with NHS esters of detectable markers, e.g., fluorescent dye-NHS, to generate platinum labeling compounds according to the invention.

Non-limiting examples of linkers useful according to the invention include: $(CH_2)n$, $(CH_2)_n(CH=CH)_mO(CH=CH)_p$ $(CH_2)_q$, $CO(CH_2)_n(CH=CH)_m(CH_2)_p$, COAr $(CH_2)_n(CH=CH)_m(CH_2)_p$, $NH_2(CH_2)_nQ$, $NH_2((CH_2)_nO)_m(CH_2)_t$ Q, $NH_2(CH_2)_mAr(CH_2)_nQ$, wherein m, n, p, q and t are integers from 0 to 8, inclusive, and m, n, p, q and t are the same or different. In the foregoing exemplary linker formulae, Q is selected from the group consisting of CONH, NHCO, —S—S—, NHCSNH, NHCSO, wherein

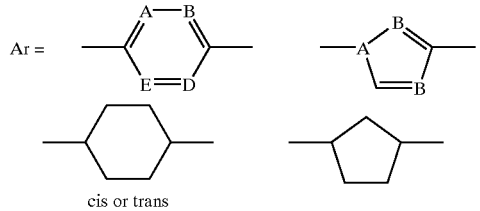

cis or trans and A, B, D, and E are the same or different and are selected from the group consisting of CH, N, O and S.

Linkers are attached either to the platinum ion (i.e., by direct coordination to a site on the platinum ion that does not participate in the cycloaliphatic diamine bridge structure) or to one of the terminal nitrogens of the cycloaliphatic diamine bridge. When linkers are attached to the platinum ion, the linker must have a reactive group that displaces the leaving group from the platinum ion, thereby attaching the linker to the platinum ion. In this case, the detectable marker, e.g., a fluorescent dye, is already attached to the opposite end of the linker, such that the reaction of the linker with the platinum compound results in a platinum labeling compound according to the invention. This scheme is further described below in "How to make a platinum labeling compound according to the invention," and in the Examples.

When the linker is to be attached to a terminal nitrogen of the cycloaliphatic diamine (the nitrogen being bound to the platinum ion), the linker can be first attached to the detectable marker (e.g., by reaction of a liker carboxylate with a dye-NHS) and the marker-linker can then be reacted with the cycloaliphatic diamine to generate a labeled cycloaliphatic diamine, which can then be reacted with platinum to generate a platinum labeling compound according to the invention. This scheme is also further described below in "How to make a platinum labeling compound according to the invention," and in the Examples.

III. How to Make Platinum Labeling Compounds According to the Invention

Standard chemical synthetic techniques known to those skilled in the art can be used to make platinum labeling compounds according to the invention. In general, the steps necessary to make such compounds include the steps of attaching a detectable marker to a nitrogen on a cycloaliphatic diamine to generate a labeled cycloaliphatic diamine, and then reacting the labeled cycloaliphatic diamine with Pt(II) to generate a Pt(II) labeling compound with a cycloaliphatic diamine bridge bearing a detectable marker on a nitrogen bound to the platinum atom. Alternatively, one can generate a Pt(II) intermediate comprising a cycloaliphatic diamine bridge structure and then react the intermediate with a detectable marker bearing an appropriate reactive group.

A standard approach acceptable for the generation of platinum labeling compounds of the invention is described in, for example, U.S. Pat. No. 5,714,327, Houthoff et al., which is incorporated herein by reference. In this approach, potassium tetrachloroplatinate is first converted to a tetraiodoplatinate. The tetraiodoplatinate is reacted with ethylenediamine, to generate a Pt(II) ethylenediamine diiodide. The diiodide is transferred to its nitrate derivative through ligand exchange, forming the Pt(II) ethylenediamine dinitrate, which is then reacted with a dye bearing an activated linker. By substituting the ethylenediamine with a cycloaliphatic diamine, one may readily adapt this method to generate platinum labeling compounds according to the invention. This method will generate monofunctional compounds in which the detectable marker is attached to a nitrogen that is not part of the aliphatic diamine stabilizing bridge, meaning that there is room for only one functional leaving group.

Figure 4:
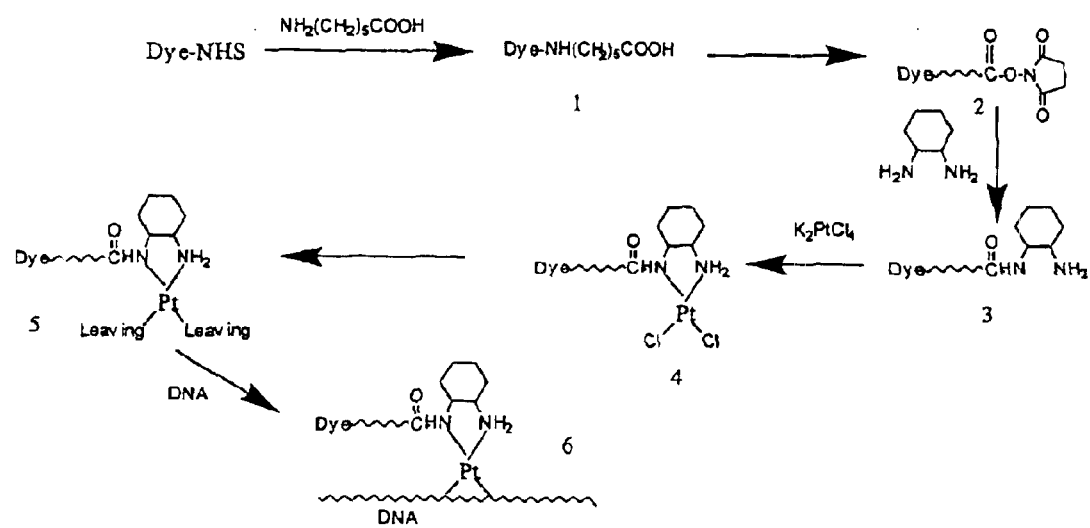
FIG. 4 shows a schematic diagram of synthetic steps for a platinum labeling compound according to the invention. The numbered intermediates or products 1–6 are referred to in Examples 1 and 2.

While the prior art method of generating platinum labeling compounds is acceptable for making compounds according to the invention, a novel method is disclosed herein which simplifies and speeds the synthetic scheme by avoiding the necessity for a ligand exchange step. The method involves the key step of directly reacting potassium tetrachloroplatinate (II) with a cycloaliphatic diamine bearing a detectable marker. The reaction forms a labeled platinum cycloaliphatic diamine dichloride. The cycloaliphatic diamine forms a stabilizing bridge and the two chloride ions serve as leaving groups available for subsequent reaction with a biomolecule. FIG. 4 shows a schematic diagram of one such reaction process.

Methods of preparing dyes or other detectable markers bearing activated groups for reaction with an amine are known in the art. Table 1 lists a number of reactive groups and their corresponding complementary functional groups which are routinely used to react with the functional groups common in biomolecules. Those reactive groups that react with amines are clearly of most particular interest. Other functional groups, such as aryl azides, react indiscriminantly with nearby residues following ultraviolet photolysis.

TABLE 1

Selected Reactive Substituents and Functional Groups Reactive Therewith

| Reactive Groups (V) | Corresponding Functional Groups |
| --- | --- |
| succinimidyl esters | amines |
| anhydrides | amines, alcohols |
| acyl azides | amines |
| isothiocyanates | amines, thiols, alcohols, phenols |
| sulfonyl chlorides, sulfonyl fluorides | amines, phenols, alcohols |
| substituted hydrazines, substituted hydroxylamines | aldehydes, ketones |
| acid halides | amino groups |
| haloacetamides, maleimides | thiols, imidazoles, phenols, amines |
| carobdiimides | carboxyl groups |
| phosphoramidite | alcohol groups |

Examples of approaches to the generation of dyes, or other detectable marker molecules, bearing reactive groups include:

a) Succinimidyl esters are typically prepared from dyes, or other detectable markers, having a carboxylic acid substituent using N-hydroxysuccinimide and dicyclohexylcarbodiimide (see below);
b) Acid chlorides are typically prepared from dyes, or other detectable markers, containing carboxylic acid substituents using oxalyl chlorides or thionyl chloride;
c) Isocyanates are typically prepared from dyes, or other detectable markers, containing amine groups using phosgene;
d) Isothiocyanates are typically prepared from dyes, or other detectable markers, having amino substituents using thiophosgene;
e) Photoaffinity labels are typically incorporated by reaction of an amine-containing dye or other detectable marker and a known photoaffinity label that also contains an amine-reactive group; and
f) Maleimido groups are typically prepared from an amine-containing dye or other detectable marker and maleic anhydride.

One skilled in the art can readily react a detectable marker containing a given amine-reactive functional group with a cycloaliphatic diamine. As a non-limiting example, one of the most commonly used coupling methods for fluorescent dyes involves reaction of a dye-succinimidyl ester with an amino group on the molecule of interest. Succinimidyl ester-dyes are prepared, for example, by reaction of N-hydroxysuccinimide (NHS) with a carboxyl group on the dye. NHS-modified dyes or isothiocyanate-modified dyes are also commercially available (e.g., from Molecular Probes, Eugene OR). If desired, a dye or other marker may be modified to have a short spacer (e.g., an alkyl chain) between the dye and the NHS active group, for example by reacting an NHS dye with 6-amino-n-caproic acid to form a dye-aminocarboxylic acid. This product is then reacted in anhydrous DMF with NHS to form a dye-NHS compound having the short spacer between the dye and the active NHS group. It is this dye-NHS compound that is then reacted with a cycloaliphatic diamine to generate a dye-labeled cycloaliphatic diamine.

Figure 5:
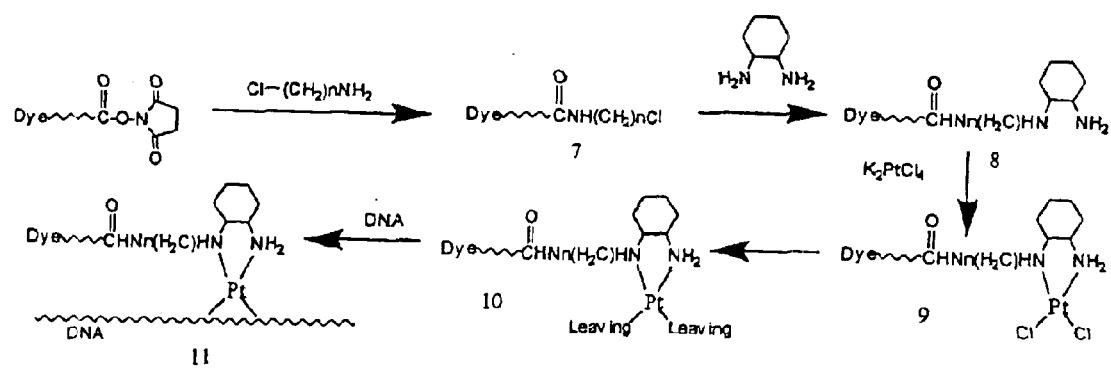
FIG. 5 shows a schematic diagram of synthetic steps for a platinum labeling compound according to the invention. The numbered intermediates or products 7–11 are referred to in Example 2.

Any of the amine-reactive functional groups noted in Table 1 or any other groups known in the art to react with amines can also be used for the attachment of a dye or other detectable marker to an aliphatic diamine useful in the generation of platinum labeling complexes described herein. For example, FIG. 5 schematically shows the reaction of 3-chloropropyl amine with the succinimidyl ester of a dye to generate an amido-dye compound that can then be reacted with a cycloaliphatic diamine. The resulting dye-labeled cycloaliphatic diamine is then directly reacted with potassium tetrachloroplatinate (II) to yield a functional platinum labeling compound, as described above.

An exemplary cycloaliphatic diamine is 1,2-diaminocyclohexan, which will result, after reaction with Pt, in a compound according to Formula 2. Generation of a labeled cycloaliphatic diamine that will give rise to platinum labeling compounds according to Formulae 1 and 3–11, is a straightforward process in which the starting cycloaliphatic diamine used in the labeling process described above is replaced by one having the ring structure and substituents necessary to provide the cyclic diamine bridge structure desired.

Following the generation of labeled cycloaliphatic diamine as described above and in the Examples herein, the novel platinum labeling compound synthetic approach disclosed herein involves the reaction of the labeled cycloaliphatic diamine with potassium tetrachloroplatinate in aqueous solution. The reaction is conducted in aqueous solution at a pH of about 3.5 (pH values from 1.5 to 5.5, inclusive are acceptable), and at about 65° C. A 20 hour reaction time is generally used, although shorter times will yield the desired product, if perhaps somewhat less efficiently. The product is a platinum cycloaliphatic diamino dichloride. The dichloride form may then be reacted with silver nitrate to generate the dinitrate form.

IV. How to Use the Platinum Labeling Compounds According to the Invention.

The platinum labeling compounds disclosed herein are useful for labeling biomolecules bearing an available site for platinum adduct formation, including, but not limited to nucleic acids and polypeptides.

A. Labeling of Biomolecules

1. Nucleic Acids.

The labeling of nucleic acids with platinum compounds according to the invention is very straightforward, and can be finished in 2–3 hours, including probe purification. A labeling compound is simply mixed with an aqueous solution of nucleic acid (DNA, RNA, PNA) and the platinum compound forms adducts via the nucleotide bases. Excess labeling compound is removed by standard means and the labeled probe is ready for use. The following protocol is recommended for the labeling of DNA (the steps are essentially the same for RNA or PNA). The labeling reaction calls for 1 $\mu$g of DNA in 25 $\mu$l of labeling buffer (10 mM Tris, 1 mM EDTA, pH 7.4). About 0.5 nmole of the platinum labeling compound is required for labeling 1 $\mu$g of DNA. The steps are as follows:

(a) Precipitate 1 $\mu$g of DNA by adding 1/10 volume of 3M sodium chloride and 2.5 volumes of absolute ethyl alcohol, keeping at –70° C. for 30 minutes, then centrifuge for 30 minutes at 12K rpm. Wash the pellet with 70% ethanol and allow it to air dry. Resuspend the pellet in 25 $\mu$l of the labeling buffer (10 mM Tris, 1 mM EDTA, pH 7.4). This step is recommended before labeling in order to remove ammonium and amine residue that will interfere with the labeling reaction. It is important that ammonium acetate not be used for the DNA precipitation, because the residual ammonium ion will interfere with the cis-Pt labeling reaction. Also, do not use carrier DNA to assist in the ethanol precipitation, as this will also interfere with the labeling reaction. cDNA made from a reverse transcription reaction should be purified from RNA and excess primers before labeling. High concentrations of Tris-HCl (>40 mM), EDTA (>5mM), Mg acetate (>100 mM), or NaCl (>100 mM), and restriction enzyme digestion buffers should also be avoided.

(b) Denature the DNA at 95° C. for 5 minutes, then snap chill on ice. Centrifuge the tube briefly to redeposit the sample to the bottom of the tube. Denaturation is not absolutely necessary, but improves labeling yield.

(c) Add 10 $\mu$l of 50% DMF to the vial containing cis-Pt labeling dye. Mix by vortexing until all of the labeling reagent goes into solution. The stock solutions may be stored at 4° C. for up to few weeks. It is important that the DMF used be of high purity, because standard grade DMF contains some amine, which interferes with the labeling reaction. For example, DMF obtained from Aldrich, (Catalog No. 22705-6) works well for this purpose. Stock solutions of platinum labeling compound in 50% DMF are stable at 4° C. for several months (in the dark).

(d) Combine the platinum labeling compound solution with the denatured DNA solution. Centrifuge the tube briefly to redeposit the sample to the bottom of the tube.

(e) Incubate the reaction at 80° C. for 30 minutes. Cool the reaction mixture in an ice bath, then centrifuge.

(f) The labeled DNA can then be purified by column chromatography, most conveniently a spin column. Commercially available columns include (e.g., Stratagene's NucTrap™ Probe Purification Column, Qiagen's QIAquick™ Nucleotide Removal Kit, and Waters' Sep-Pak™ cartridge (C18 column, 3 ml)). Alternatively, the labeled DNA can be purified by standard ethanol precipitation or by reverse HPLC.

Figure 6:
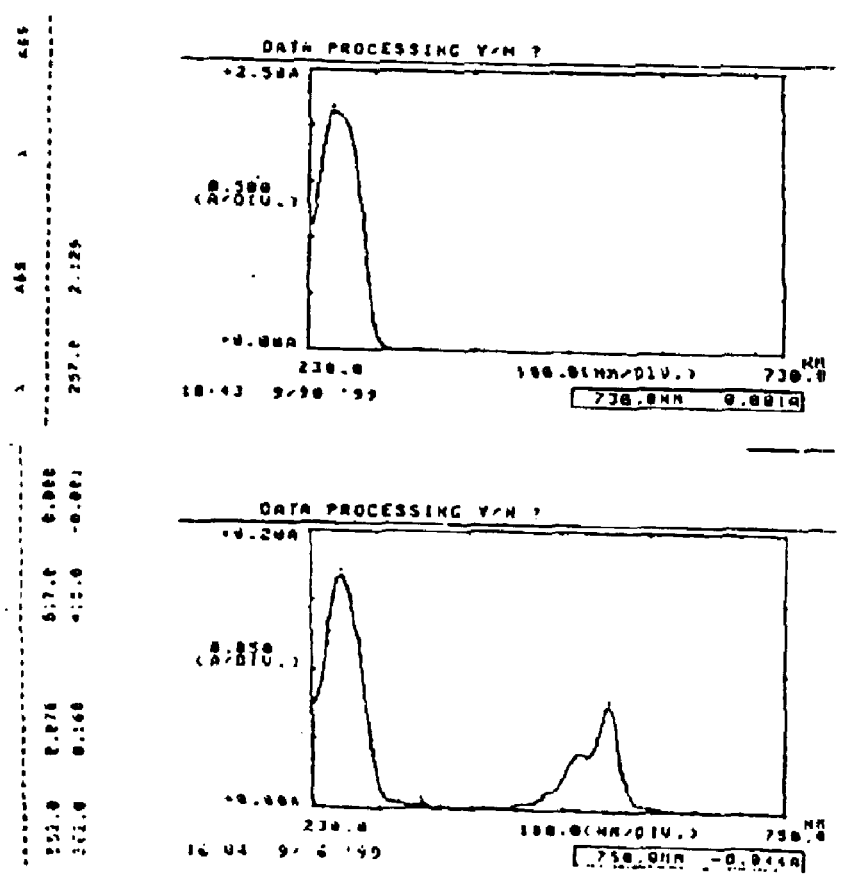
FIG. 6 shows UV absorption spectra of an unlabeled DNA probe and a Cy3-platinum labeling compound-labeled DNA probe. Top, unlabeled probe; bottom, labeled probe.

It was found that a synthetic DNA 73-mer labeled using a platinum labeling compound of the invention had a shift in maximum UV absorption from 257 nm to 262 nm (FIG. 6). The interaction of cis-DDP with DNA has previously been noted to shift the UV absorption maximum of DNA from 259 nm to 264 nm, most likely through platinum association with the base (Horacek et al., 1971, Biochim. Biophys. Acta 254: 341). The concentration of the labeled DNA probe is determined by UV absorption at 260 nm ($A_{260}$) using the formula C=($A_{260}$–$A'_{260}$)×30 ng/$\mu$l, where $A_{260}$ and $A'_{260}$ are the UV absorption, at 260 nm, of labeled DNA and the free dye, respectively.

Probes can be generated from purified DNA, synthetic oligonucleotides, or from cDNA to probes generated by reverse transcription of RNA (e.g., mRNA) templates. In order to label a cDNA probe, one first synthesizes a reverse transcript using, for example, 20 $\mu$g of an RNA template, oligo-dT primer and reverse transcriptase (e.g., StrataScript™ reverse transcriptase, Stratagene, La Jolla, Calif.). The reaction products are then treated with sodium hydroxide to hydrolyze the RNA template, and the hydrolized RNA and unused primers are removed (e.g., by spin column chromatography over an S-100 matrix column (Sigma, St Louis, Mo.). The collected cDNA is then ethanol precipitated and reacted with platinum labeling compound as described above, before a final ethanol precipitation to remove unbound labeling compound.

2. Polypeptides.

Similar to the process used to label nucleic acids, the process for labeling polypeptides is straightforward. The general steps include mixture of a platinum labeling compound with a polypeptide to be labeled and separation of labeled polypeptide from excess labeling complex. The following describes the steps used to label a polypeptide (e.g., an antibody).

The polypeptide to be labeled is prepared in low concentration Tris buffer, typically about 20 mM Tris, and at a polypeptide concentration of about 1 mg/ml. The pH of the polypeptide solution is adjusted to the range of pH 9 to pH10 (using, for example, carbonate buffer, pH 10). A solution of 1 $\mu$g/ml platinum labeling compound is prepared in methanol and mixed with an equal volume of 40 mM Tris, pH 9.5, yielding a 20 mM Tris solution having 500 ng labeling compound per ml. Equal volumes (e.g., 1 ml) of the platinum labeling compound solution and the polypeptide solution are mixed and incubated at room temperature for about 4 hours, followed by incubation at 4° C. for about 16 hours. This mixture provides an approximately 1:100 molar ratio of polypeptide to labeling compound when the polypeptide is an antibody. This 1:100 molar ratio should be maintained when using polypeptides of higher or lower molecular weight. Unbound platinum labeling compound is removed through size-exclusion column chromatography (e.g., using Sephadex G-25) and the labeled polypeptide is ready for use.

B. How to Use Probes Labeled with Platinum Labeling Compounds.

Probes detectably labeled with platinum labeling compounds are useful in any method or assay that calls for a probe labeled with the selected detectable marker. Primary among the assays that are well suited for probes labeled according to the invention are nucleic acid hybridization assays and assays using labeled antibodies or other specific binding molecules. In general, a probe labeled with a platinum labeling compound of the invention is used in the same manner as a probe labeled through prior art means. The advantage in using probes labeled using platinum labeling compounds is primarily one of convenience and efficiency in the labeling. Therefore, once a probe is labeled according to the invention, the steps involved in using it are essentially the same as those steps known in the art for using any probe labeled with that detectable marker.

Nucleic acids labeled with platinum labeling compounds are useful in diagnostic hybridization assays for viral, bacterial or fungal pathogens or other parasites, hybridization-based assays to determine an individual's genotype with respect to known polymorphisms or disease-linked gene sequences, and hybridization-based assays for gene expression. The hybridization characteristics of a nucleic acid probe labeled using a platinum labeling compound do not vary dramatically from those of a probe labeled with, for example, a radiolabeled nucleotide. The presence of platinum adducts has been reported to slightly lower the melting temperature ($T_m$) of nucleic acid hybrids. It is well within the ability of one of skill in the art to adjust hybridization conditions in order to compensate for a slight decrease in $T_m$. That is, the platinum labeling adduct does not significantly alter the standard way in which one performs nucleic acid hybridization. Therefore, standard solutions and conditions can generally be used for hybridization assays using probes labeled with platinum labeling compounds according to the invention.

One area where significant differences do arise in the conditions used for hybridization and detection does not actually result from the platinum adduct formation itself, but rather, is the result of differences in the detectable markers one attaches to the nucleic acid probe. For example, when biotin-labeled probes are used, polyvinylpyrrolidone, a constituent of Denhardt's solution, should be omitted from the hybridization solution. As another simple example, when the probe is labeled with a fluorescent marker, it should generally be protected from bright light. These differences and others are known to those skilled in the use of the various detectable markers one may choose to attach to a probe molecule (whether the probe is a nucleic acid, a polypeptide or another molecule) through a platinum labeling compound according to the invention.

Polypeptide probes labeled with platinum labeling compounds according to the invention are used in the same manner as polypeptides labeled with other detectable markers. In particular, a polypeptide, such as an antibody, labeled with a fluorescent marker using a platinum labeling compound, is used in the same manner as a polypeptide labeled with the same fluorescent marker using methods in the prior art. Again, the primary advantage of using the labeling compounds of the invention to label a polypeptide is the ease and efficiency of the labeling reaction. Therefore, the methods of using the labeled polypeptide probe will not differ significantly from those of using that polypeptide labeled with the same marker via a method known in the prior art. Again, the exception to this general rule is that probing and detection techniques will vary depending upon the nature and identity of the detectable marker. One knowledgeable in the use of probes labeled with a given selectable marker will be able to adjust the probing and detection methods as necessary for that marker.

Probes labeled with platinum labeling compounds according to the invention are useful for Northern and Southern hybridization analyses. The hybridization conditions are essentially the same as those known in the art for each method. As noted above, aside from a slight decrease in Tm, the differences that do arise are related to the nature of the detectable marker. The steps for both Northern and Southern Blot analysis are essentially as follows: 1) pre-hybridize the membrane at 42° C. for 30 minutes to overnight in hybridization solution (e.g., 5×SSC, 5×Denhardt's reagent (0.1% (w/v) Ficoll 400, 0.1% (w/v) polyvinylpyrrolidone, 1 mg/ml bovine serum albumin (fraction V)), 50% formamide, 1% SDS and 100 µg/ml denatured salmon sperm DNA); 2) denature probe labeled with a platinum labeling compound for 5 minutes at 95° C. and quick chill; 3) add denatured probe to hybridization solution to final concentration of about 10 ng/ml and apply the probe mix to the filter; 4) hybridize overnight at 42° C.; 5) wash the filter 2×15 minutes at room temperature in 2×SSC/0.1% SDS; 6) wash the filter 2×15–30 minutes at 68° C. in 0.5×SSC, 0.1% SDS. Those skilled in the art will realize that the stringency of the hybridization largely depends upon the wash conditions, both temperature and salt concentration. Therefore, it is well within the ability of one skilled in the art to modify the wash conditions to achieve a desired level of stringency. The final step, detection of bound probe will necessarily vary depending upon the nature and identity of the detectable marker. Markers that are directly detectable can be detected by that direct means (e.g., fluorescence), and those that are indirect can be detected following the addition of the appropriate co-factor (e.g., a chromogenic substrate or an enzyme-labeled binding partner and substrate).

Probes labeled using platinum labeling compounds according to the invention are also useful for in situ hybridization analyses. Again, the conditions are similar to those used with nucleic acid probes labeled using other means of detectable marker attachment (Standard conditions are reported in, for example, *Short Protocols in Molecular Biology, a Compendium of Methods from Current Protocols in Molecular Biology*, 3$^{rd}$ Edition, 1992, Ausubel et al., Eds, John Wiley & Sons, Inc., New York, pp 14-1 to 14-49). Those skilled in the art of in situ hybridization (e.g., DISH or RISH) can readily adjust the hybridization and wash conditions of standard assays to function with probes labeled according to the invention. As with other uses of probes labeled with platinum labeling compounds according to the invention, differences in the nature and identity of the detectable marker used can be taken into consideration by one skilled in the art of using that particular detectable marker when performing in situ hybridization.

Probes labeled using platinum labeling compounds according to the invention are particularly useful for array and microarray-based assays of both nucleic acid and protein or tissue samples. Examples include array-based expression assays and array-based sequencing methods (e.g., sequencing by hybridization, SBH). Through use of different probes labeled with distinguishable markers, such as spectrally distinguishable fluorophores, combinations of probes can be applied to the array at the same time in order to examine co-expression or differential expression on the same array. Again, standard probing and washing conditions can be used with adjustments made for differing detectable markers.

In one embodiment, the invention encompasses kits for the labeling of biomolecules with platinum labeling compounds according to the invention. Kits will contain one or more platinum labeling compounds according to any of Formulae 1–11 . Platinum labeling compounds bearing any of an array of different detectable markers can be provided in a kit. Kits can additionally contain 50% DMF of sufficient purity for the platinum compound labeling reaction, to be used in resuspending the platinum labeling compound, as well as labeling buffer (10 mM Tris, 1 mM EDTA, pH 7.4), packaging materials and instructions for using the kit.

EXAMPLES

All chemicals and solvents used in the following examples were obtained from Aldrich (Milwaukee, Wis.) unless otherwise noted. A Shimadzu SCL-10Avp HPLC system (Tokyo, Japan) consisting of dual LC-10 ATvp pumps and an SPD-M10Avp photodiode array detector was used to monitor the synthetic reactions. Analysis was accomplished by gradient elution through a C18 column (5 μ, AQUA, 125 A, 22×250 mm, Phenomenex, Torrance, Calif.) using 0.1 M triethylammonium acetate (A) and 60% acetonitrile (B) as solution. The column was eluted for 5 minutes at 10% B, followed by a gradient of up to 80% B over 40 minutes. Mass spectra were performed using a Perkin Elmer PE SCIEX API 100 with ion spray (NuMega Lab., San Diego, Calif.). All reactions were carried out in the dark. In the following Examples, the bold numbers in parentheses refer to the structures shown in schematic FIGS. 4, 5 and 7, referenced in the text.

Example 1

Preparation of Tetramethylrhodamine-6-carboxamido Hexanoic Acid (1)

6-carboxytetramethylrhodamine, succinimidyl ester (TAMRA, 30 mg, Molecular Probes, Eugene, Oreg.) was resuspended in 1 ml of anhydrous DMF, mixed with 6-amino-n-caproic acid (29.8 mg) in 0.1 M sodium borate buffer (3 ml, pH9). The reaction mixture was shaken at room temperature for 4 hours, purified through HPLC, yield 30 mg of compound (1) of FIG. 4, MS m/z 545 (M+1).

Example 2

Synthesis of Platinum Labeling Complexes

A. Preparation of 1'-Amino-2' (Tetramethylrhodamine-6-carboxamido Hexanoylamino)-transcyclohexane (3).

Compound (1) (30 mg) was resuspended in 1 ml of anhydrous DMF, mixed with 1 ml of anhydrous DMF containing 30 mg of N,N'-dicyclohexylcarbodiimde (DCC, Pierce, Rockford, Ill.) and 130 mg of N-hydroxysuccinimide. The reaction mixture was stirred at room temperature for 16 hours, trans-1,2-diaminocyclohexane (620 mg) in 4 ml of DMF was added in, stirring overnight. The same volume of water was added into the reaction mixture, changing the color from pale-red/gray to dark red. The product was isolated through HPLC, giving (3), 24.5 mg. MS m/z 641 (M+1). Derivatives of (3) with other dyes were made through the same procedure, characterized by MS m/z: Cy5, 754 (M); FAM, 586(M+1); Bodipy, 643 (M+1).

B. Preparation of Platinum (TAMRA-cyclohexanediamine)-dichloride (4).

Potassium tetrachioroplatinate (II) (10 mg) was suspended in 1 ml of water, and pH was adjusted to 3.5. Compound (3) (15 mg) was added into the platinum solution, and heated at 65° C. for 20 hours. The pH of the mixture was raised to 8.5 by the addition of sodium hydroxide solution. An aliquot was analyzed by MS. MS m/z: 906 (M+1). Derivatives of (4) with other dyes were made through the same procedure, MS for Cy3: 997 (M+1).

C. Preparation of Platinum (Cy3-cyclohexanediamine)-dinitrate (5).

The Cy3 derivative of compound (4) (1.2 mg) was added into 0.8 ml of 1 M silver nitrate solution in DMF. A white precipitate was formed. The reaction mixture was stirred at room temperature for 6 hours, and the precipitate was removed under centrifuge. An aliquot of the clear solution was analzyed by MS: m/z 1062 (M+H$_2$O).

D. Preparation of (Tetramethylrhodamine-5 and 6-carboxamido) Propyl Chloride (7).

3-Chloropropylamine (184 mg) in 2 ml of 0.1 M sodium borate buffer (pH 9) was added to a mixture of 5- and 6-carboxytetramethylrhodamine, succinimidyl ester (TAMRA NHS ester, 75 mg, Molecular Probes) in 1 ml of anhydrous DMF. The mixture was stirred at room temperature overnight. The products were isolated through HPLC, yielding 72 mg of (7). MS m/z: 504 (M−1).

E. Preparation of Platinum (TAMRA-cyclohexanediamine)-dichloride(9).

35 mg of compound (7) was dissolved in 1.5 ml of trans-1,2-diaminocyclohexane. The dark red color of compound (7) faded away. The solution was heated at 80–82° C. for 6 hours, and the solvent was removed under vacuum, yielding (a) MS m/z: 850 (M−1).

F. Preparation of Platinum (TAMRA-cyclohexanediamine)-dinitrate (10).

Compound (10) was made through the same procedure for (5). MS m/z: 1016 (M+Ag$^+$).

Figure 7:
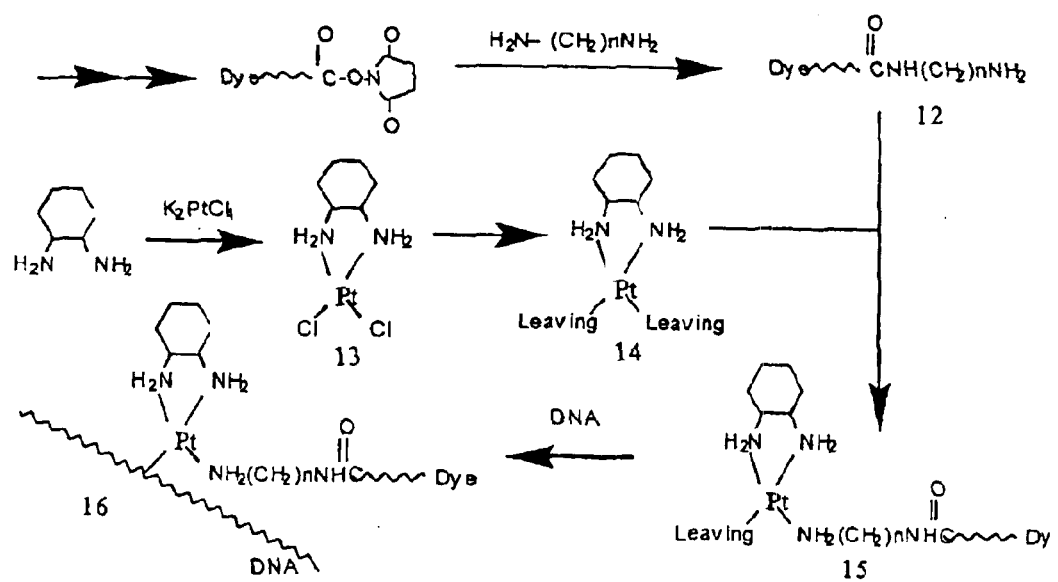
FIG. 7 shows a schematic diagram of synthetic steps for a platinum labeling compound according to the invention. The numbered intermediates or products 12–16 are referred to in Example 2.

The synthetic approach detailed in sub-sections G–I are shown schematically in FIG. 7.

G. Preparation of (Cy5-hexanoylamido)-hexaneamine (12).

Cy5 monofunctional dye (1 mg, Amersham, UK) in 400 ul of anhydrous DMF was added into 1.3 ml of 0,1 M sodium borate buffer (pH9) containing 10 mg of 1,6-hexanediamine. The reaction mixture was stirred at room temperature for 2.5 hours, the product was purified through HPLC, giving 1 mg of (12). MS m/z: 755 (M−1). It's derivative of Cy3 was obtained by the same method, MS m/z: 729 (M−1).

H. Preparation of Platinum Cyclohexanediamine Dinitrate (14).

Potassium tetrachloroplatinate (II) (460 mg) was resuspended in 4 ml of water, adjusted pH to 3.5. To the solution was added trans-1,2-diaminocyclohexane (126.5 mg), a precipitate was formed. The pH of the mixture was brought to 3.5 with 1N hydrochloric acid, in a total volume of 7 ml. The reaction solution was heated to 65° C. for 17 hours. A yellow precipitate was formed, the pH of the mixture was raised to 8.5 with 1N sodium hydroxide. The precipitate was collected by centrifuge, washed with water (3×10 ml), ethyl acetate (1×10 ml), then air dried. The pale yellow solid obtained was resuspended into 10 ml of anhydrous DMF, and mixed with 2 equivalents of 1M silver nitrate in DMF. A white precipitate was formed, the clear solution was used for further reaction. MS m/z: 369 (M−NO$_3$).

I. Preparation of Platinum Cyclohexanediamine-Cy3-nitrate (15).

Cy3 derivative of compound (12) (1.24μ mole) was resuspended in 400 μl of DMF, mixed with 9 μmole of compound (14) in 1 ml of DMF. The reaction solution was stirred at room temperature for 3 hours., the product (15) was purified through HPLC. MS m/z: 1208 {M(Ag salt)−1}. Starting from 1 mg of Cy3 monofunctional dye through intermediate (12) the final product cis-Pt-Cy3 labeling reagent (15) was packaged into 100 vials, each vial containing 0.5 nmole of (15), which is enough for labeling 1–2 μg of natural DNA or cDNA.

A number of different fluorophores, including Cy3, Cy5, TAMRA, BODIPY and FAM have been used as detectable markers on platinum labeling compounds represented by structures (5), (10) and (15) using techniques directly analogous to those reported herein.

Example 3

Oligonucleotide Labeling with Platinum Labeling Compounds of the Invention

A synthetic oligonucleotide (HUCL-3, 73-mer, 5'-AAACCCGGGAGCTCGAATTCC CTATAGT-

Figure 8:
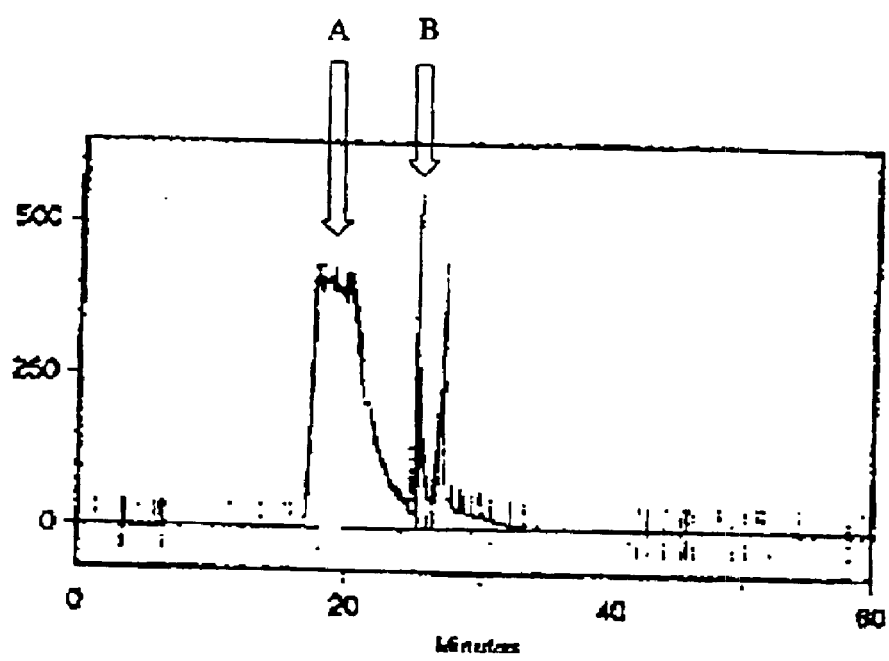
FIG. 8 shows reverse phase HPLC separation of Cy5-labeled oligonucleotide from free Cy5-platinum labeling compound. Peak A is Cy5-labeled HUCL-3 oligonucleotide (73-mer). Peak B is free dye-platinum labeling compound.
Figure 9:
FIG. 9 shows agarose gel electrophoretic separation of Cy3-platinum labeled DNA oligonucleotide versus free dye-platinum labeling reagent and Cy3-primer-labeled oligonucleotide.

GAGTCGTATITAAATTCGTAATCATGT-CATAGCTGTTTCCTGTGTG 3' (SEQ ID NO:1), 17 n mole) was resuspended in 250 µl of labeling buffer (10 mM Tris, 1 mM EDTA, pH 7.4), denatured at 95° C. for 5 minutes, then cooled in an ice-bath. Cis-Pt-Cy3 labeling reagent (compound (5), 34 nmol) in 250 µl of labeling buffer was added to the above solution. The reaction mixture was heated at 80° C. for 30 minutes and the labeled DNA oligonucleotide was isolated by HPLC (FIG. 8). Gel electrophoresis versus free labeling reagent and an aliquot of the same oligonucleotide labeled using a Cy3-labeled primer showed that the labeled oligo DNA was free from cis-Pt-Cy3 labeling dye (FIG. 9).

Example 4

Optimization of Labeling Reaction Conditions

A series of oligonucleotide labeling reactions was conducted in order to determine the optimal reaction parameters. Table 2 shows that satisfactory results can be accomplished by reaction at 80° C. for 30 minutes using two fold excess of platinum labeling compound, with a labeling yield of 90–95% upon HPLC analysis. FIG. 8 shows the result of reverse HPLC analysis of a labeling reaction carried out under these conditions. Peak A represents Cy-5 labeled probe (HUCL-3, a 73-mer), and peak B represents free Cy-5 platinum labeling compound. It is helpful, but not absolutely necessary, to run a similar series of labeling reactions (possibly over a narrower range of times and temperatures centered roughly about the 80° C., 30 minute parameters) with any new probe sequence in order to optimize the labeling conditions for that probe.

TABLE 2

Labeling Condition Optimization

| Reaction # | Temperature | time | cis-Pt-dye/DNA | labeling yield |
| --- | --- | --- | --- | --- |
| H2068 | 37° C. | 20 hr. | 5.5/1 (mol/mol) | 60% |
| H2071 | 65 | 2.5 hr. | 5.5/1 | >65 |
| H2073 | 65 | 1.0 hr. | <3/1 | 50 |
| H2074 | 65 | 1.0 hr. | <2/1 | 45 |
| H2082 | 37 | 48 hr. | <2/1 | 60 |
| H2084 | 65 | 1.0 hr. | 0.07/1 | >70 |
| H2088 | 65 | 1.0 hr | 2/1 | 58 |
| H2096 | 80 | 15 min. | 15/1 | 40 |
| H2098 | 80 | 1.0 hr. | 39/62 | 80 |
| H2099 | 80 | 1.0 hr. | 2/1 | >90 |
| H2103 | 80 | 25 min. | 2/1 | 95 |
| H2107 | 80 | 30 min. | 2/1 | >95 |

Figure 10:
FIG. 10 shows agarose gel electrophoretic separation of Cy3-platinum labeled cDNA (lane B) versus cDNA fluorescently labeled through allylamine modified nucleotides (lane A) and cDNA labeled with a Cy3-labeled primer (lane C).

Example 5 cDNA Labeling with a Platinum Labeling Compound According to the Invention cDNA samples generated by reverse transcription of 20 µg of total RNA were fluorescently labeled using three different approaches: 1) reaction of incorporated allyl-amine dUTP with Cy3-NHS; 2) reaction with Cy3 platinum labeling compound (Cy3 labeling compounds used are those designated structures in FIG. 4 and structures 10 and 15 in FIG. 5); and 3) incorporation of a Cy3-labeled primer. The platinum labeling was performed as described herein, by treating the reverse transcription product with alkali, separating the cDNA from the hydrolyzed RNA and the primer molecules, ethanol precipitation, reaction with Cy3-platinum labeling compound, and final re-precipitation. The results of agarose gel electrophoresis are shown in FIG. 10: Lane A, allyl-amine-labeled cDNA; Lane B, platinum labeling compound-labeled cDNA; and Lane C, cDNA labeled with a labeled primer. The labeled product compares favorably with the product incorporating a fluorescently labeled reverse transcription primer. Table 3 details the time required to generate a probe as shown in lane B of FIG. 10.

TABLE 3

Time Consumed for cDNA Labeling from RT Reaction

| RT reaction | 65 min. |
| --- | --- |
| Hydrolysis RNA | 10 min. |
| Spin column | 5 min. |
| cDNA ethanol precipitation | 45 min. |
| cis-Pt-dye coupling | 35 min. |
| Ethanol precipitation of labeled cDNA | 45 min. |
| Total | 205 min. |

Example 6

Figure 11:
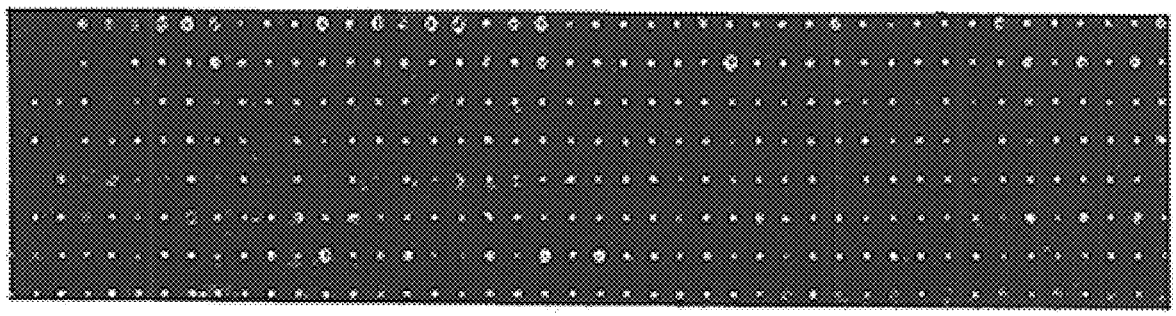
FIG. 11 shows the results of a microarray hybridization assay using either a Cy5-primer-labeled oligonucleotide probe (top) or a Cy5-platinum-labeled oligonucleotide probe (bottom).
Figure 11:
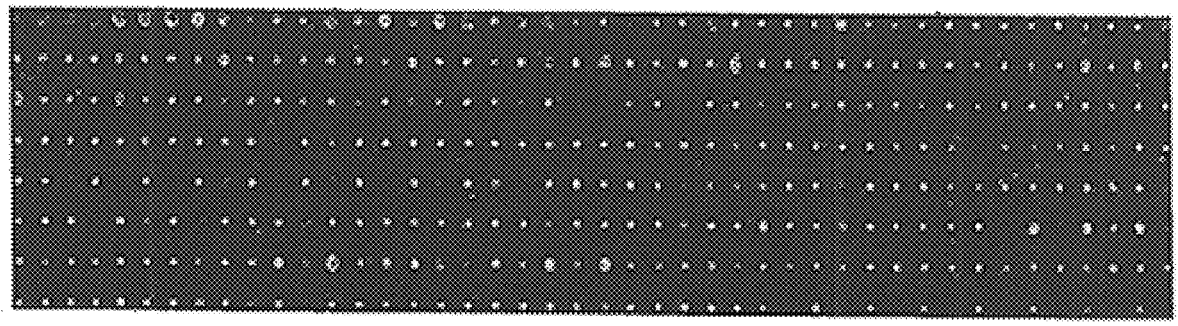

Microarray Hybridization with an Oligonucleotide Probe Labeled with a Platinum Labeling Compound Platinum labeling compound (5)-labeled HUCL-3 oligonucleotide (200 ng, labeled as in Example 3) was mixed with 30 µl 20×SSC, 1 µl Salmon Sperm DNA (10 µg/µl), 1 µl tRNA (4 µg/µl),1 µl poly $A_{40-60}$ (8 µg/µl) and 0.5 µl 10% SDS. 6 µl of the above mixture was heated at 99° C. for 2 minutes, cooled to 45° C. and placed onto a microarray and hybridized at 60° C. overnight. The slide was washed 5 minutes with 0.5×SSC, 0.01% SDS at room temperature, rinsed with water, spin dried, then scanned using a Gene Pix 4000A Scanner (Axon Instrument, Foster City, Calif.). The chip hybridized with this probe showed a clear, specific image (FIG. 11, bottom) with a high signal to background ratio.

Figure 12:
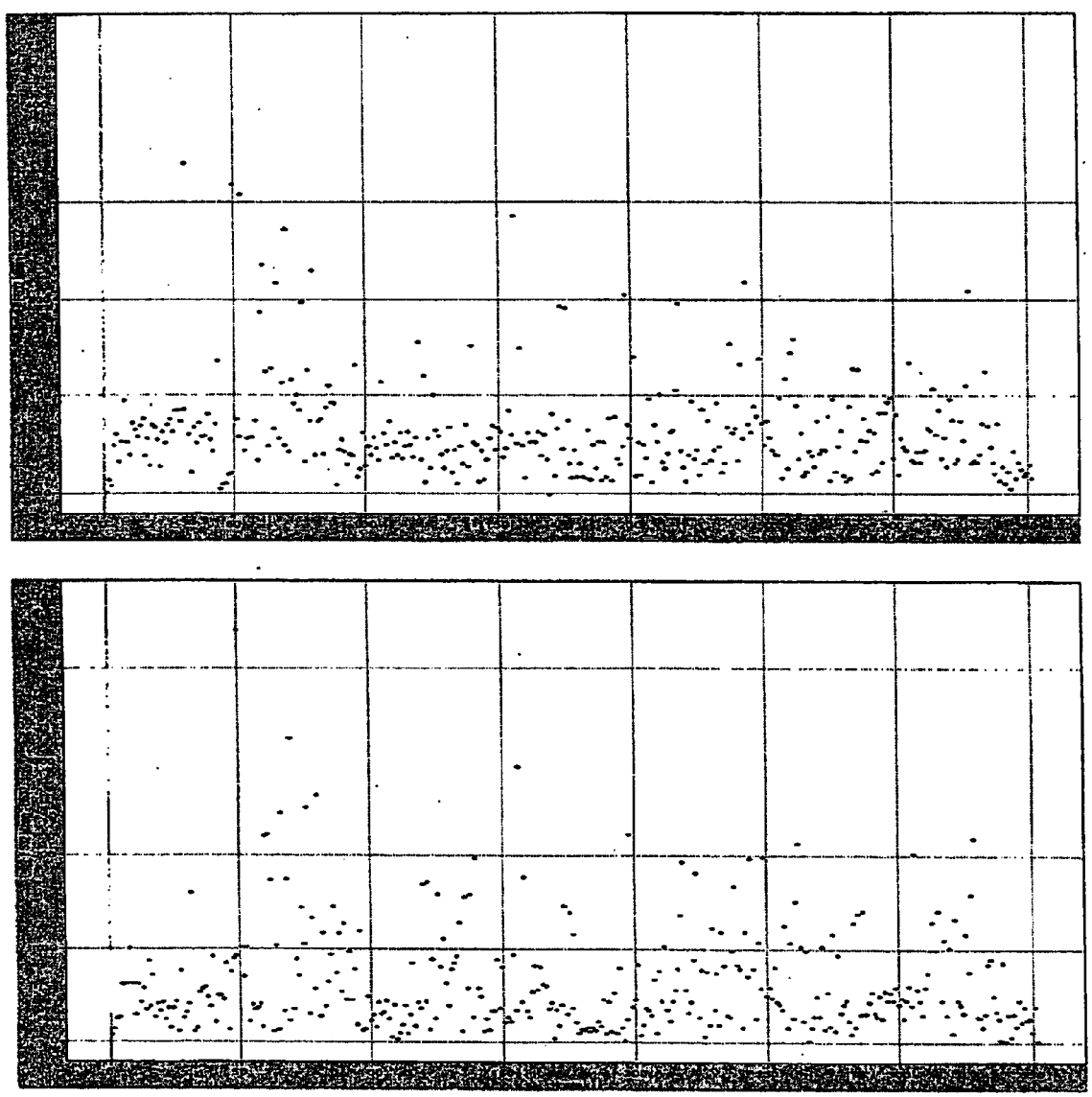
FIG. 12 shows the intensity index of each spot on the oligonucleotide-probed microarray shown in FIG. 11. Top, Cy5-primer-labeled oligonucleotide probe; bottom, Cy5-platinum-labeled oligonucleotide probe.

The same probe was hybridized to GeneConnection Discovery MicroArray metagrid 2 (Stratagene, La Jolla, Calif.). The fluorescent intensity for each DNA spot on the array is remarkably similar to the corresponding spot hybridized with a 5'-Cy3 labeled HUCL-3. FIG. 12 shows the index intensity of each spot on the array.

Example 7

Figure 13:
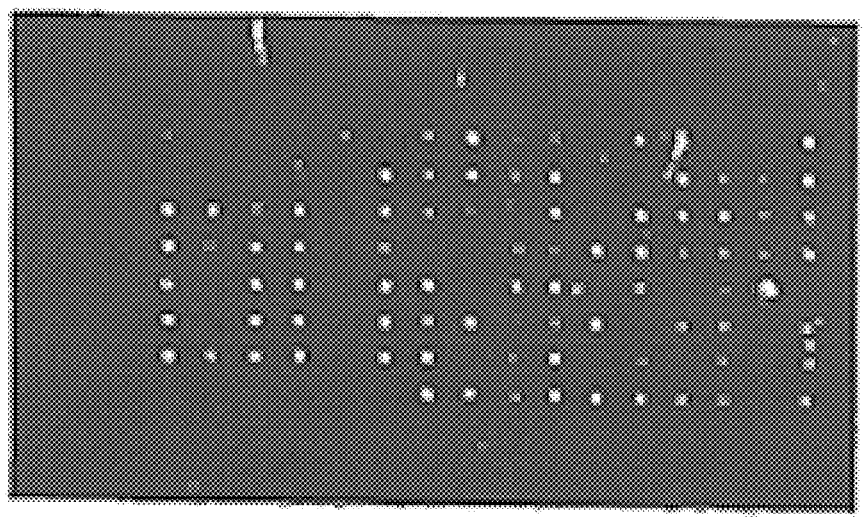
FIG. 13 shows the results of a microarray hybridization assay using Cy3-platinum-labeled cDNA on a HeLa 2 microarray.

Probing a Microarray with a cDNA Labeled with a Platinum Labeling Compound According to the Invention Ethanol precipitated total RNA (20 µg) was resuspended in 22 µl DEPC-treated distilled water and added to 3 µl of A. thaliana mRNA and 2 µl of $dT_{18}$ (500 µg/µl). The mixture was heated at 70° C. for 10 minutes and cooled on ice. 4 µl of 10×StataScript buffer, 1 µl of 20×dNTP mixture, 3 µl of 0.1 M DTT, 1 µl of Rnase block and 2 µl of StataScript (50 U/µl) were added and incubated at 42° C. for 25 minutes. Another 2 µl of StataScript (50 U/µl) was added and incubated at 42° C. for 35 minutes. 15 µl of 1M sodium hydroxide was added, and the solution and heated to 70° C. for 10 minutes. After cooling down to room temperature, the solution was neutralized with 1 M hydrochloric acid. The hydrolyzed RNA and unused primers were removed using an S-100 spin column (Sigma) and the collected cDNA was ethanol precipitated. The purified cDNA was resuspended in 15 µl of labeling buffer, added to a vial containing Cy3- platinum labeling compound in 5 μl of 50% DMF and incubated at 80° C. for 30 minutes. After ethanol precipitation, the labeled cDNA was hybridized with a HeLa 2 microarray slide as described above for the Discovery Microarray. Results are shown in FIG. 13.

OTHER EMBODIMENTS

While this invention has been particularly shown and described with references to preferred embodiments thereof, it will be understood by those skilled in the art that various changes in form and details may be made therein without departing from the scope of the invention encompassed by the appended claims. All patents, patent applications, and published references cited herein are hereby incorporated by reference in their entirety.

What is claimed is:

1. A composition comprising the formula:

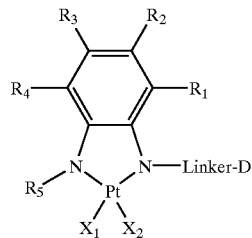

wherein:

$R_1$–$R_5$ may be the same or different and are independently selected from the group consisting of H, alkyl (1 to 10 carbon atoms), benzyl, sulfonate, phosphonate, $NO_2$, $CF_3$, halogen, O—$R_6$, —(C=O)O$R_6$, or —OCH$_2$(C=O)$R_6$ and a salt, wherein $R_6$ is a straight or branched, saturated or unsaturated, substituted or unsubstituted alkyl having 1–10 carbons;

$X_1$ and $X_2$ may be the same or different and at least one of $X_1$ or $X_2$ is a leaving group; and linker is a moiety joining a nitrogen to a detectable marker, D.

2. The composition of claim 1, wherein said leaving group is selected from the group consisting of $NO_3$, halogen CN, OCOR$_7$, OCO-Phenyl, OCOCH$_2$OC(Phenyl)$_3$, O-Trityl and 3,5-demethyl-phenyl-4-sulfate, wherein $R_7$ is selected from the group consisting of H, methyl, benzyl, sulfonate, phosphonate, $NO_2$, $CF_3$, halogen, O—$R_6$, —(C=O)O$R_6$, —OCH$_2$(C=O)$R_6$ and a salt.

3. The composition of claim 1 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p. q and t are integers from 0 to 8, inclusive, and m, n, p, q and t are the same or different, wherein Q is selected from the group consisting of CONH, NHCO, —S—S—, NHCSNH, NHCSO, wherein

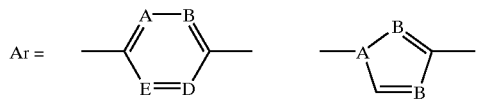

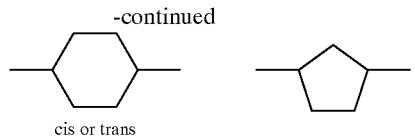

cis or trans and A, B, D, and B are the same or different and are selected from the group consisting of CH, N, O and S.

4. The composition of claim 1 wherein the detectable marker, D, is selected from the group consisting of a fluorophore, a chromophore, a radiolabel, an enzyme and an affinity tag.

5. A nucleic acid comprising a composition of claim 1.

6. The nucleic acid of claim 5 wherein said composition forms a non-covalent adduct with said nucleic acid.

7. A probe comprising a composition of claim 1.

8. A method of labeling a nucleic acid, said method comprising the step of contacting a composition of claim 1 with said nucleic acid.

9. A method of probing a nucleic acid array, said method comprising the steps of contacting said array with a probe of claim 6 and detecting signal from said detectable marker.

10. A composition comprising the formula:

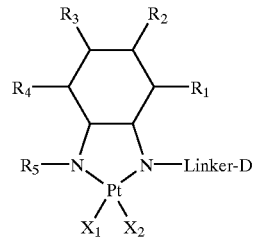

wherein:

$R_1$–$R_5$ may be the same or different and are independently selected from the group consisting of H, methyl, benzyl, sulfonate, phosphonate, $NO_2$, $CF_3$, halogen, O—$R_6$, —(C=O)O$R_6$, or —OCH$_2$(C=O)$R_6$ and a salt, wherein $R_6$ is a straight or branched, saturated or unsaturated, substituted or unsubstituted alkyl having 1–10 carbons;

$X_1$ and $X_2$ may be the same or different and at least one of $X_1$ and $X_2$ is a leaving group; and linker is a moiety joining a nitrogen to a detectable marker, D.

11. The composition of claim 10, wherein said leaving group is selected from the group consisting of $NO_3$, halogen, CN, OCOR$_7$, OCO-Phenyl, OCOCH$_2$OC(Phenyl)$_3$, O-Trityl and 3,5-dimethyl-phenyl-4-sulfate, wherein $R_7$ is selected from the group consisting of H, methyl, benzyl, sulfonate, phosphonate, $NO_2$, $CF_3$, halogen, O—$R_6$, —(C=Q)O$R_6$, —OCH$_2$(C=O)$R_6$ and a salt.

12. The composition of claim 10 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein Ar = 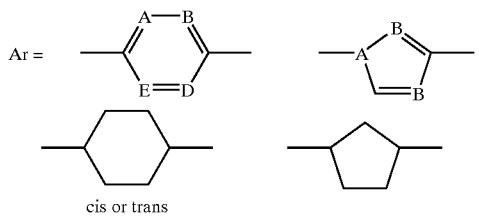

cis or trans and A, B, D, and E are the same or different and are selected from the group consisting of CH, N, O and S.

13. The composition of claim 10 wherein the detectable marker, D, is selected from the group consisting of a fluorophore, a chromophore, a radiolabel, an enzyme and an affinity tag.

14. A nucleic acid comprising a composition of claim 10.

15. The nucleic acid of claim 14 wherein said composition fonus a non-covalent adduct with said nucleic acid.

16. A probe comprising a composition of claim 10.

17. A method of labeling a nucleic acid, said method comprising the step of contacting a composition of claim 10 with said nucleic acid.

18. A method of probing a nucleic acid array, said method comprising the steps of contacting said array with a probe of claim 15 and detecting signal from said detectable marker.

19. A composition comprising the formula:

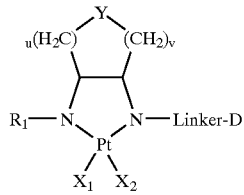

wherein

Y is selected from the group consisting of O, S, and C;

$R_1$ is selected from the group consisting of H, methyl, benzyl, sulfonate, phosphonate, $NO_2$, $CF_3$, halogen, O—$R_2$, —(C=O)O$R_2$, —OCH$_2$(C=O)$R_2$, and a salt, wherein $R_2$ is a straight or branched, saturated or unsaturated, substituted or unsubstituted alkyl having 1–10 carbons;

$X_1$ and $X_2$ are the same or different and at least one of $X_1$ or $X_2$ is a leaving group;

linker is a moiety joining a nitrogen to a detectable marker, D, and u and v are the same or different and are an integer from 1 to 10.

20. The composition of claim 19, wherein said leaving group is selected from the group consisting of $NO_3$, halogen, CN, OCOR$_3$, OCO-Phenyl, OCOCH$_2$OC(Phenyl)$_3$, O-Trityl and 3,5-dimethyl-phenyl-4-sulfate, wherein $R_3$ is selected from the group consisting of H, methyl, benzyl, sulfonate, phosphonate, $NO_2$, $CF_3$, halogen, O—$R_2$, —(C=O)O$R_2$, or —OCH$_2$(C=O)$R_2$ and a salt.

21. The composition of claim 19 wherein said linker is selected from the group consisting of: $(CH_2)n$, $(CH_2)_n$ $(CH=CH)_mO(CH=CH)_p(CH_2)_q$, $CO(CH_2)_n(CH=CH)_m$ $(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein Ar = 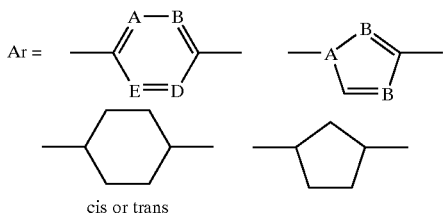

cis or trans and A, B, D, and E are the same or different and are selected from the group consisting of CH, N, O and S.

22. The composition of claim 19 wherein said detectable marker, D, is selected from the group consisting of a fluorophore, a chromophore, a radiolabel, an enzyme and an affinity tag.

23. A nucleic acid comprising a composition of claim 19.

24. The nucleic acid of claim 23 wherein said composition fonns a non-covalent adduct with said nucleic acid.

25. A probe comprising a composition of claim 19.

26. A method of labeling a nucleic acid, said method comprising the step of contacting a composition of claim 19 with said nucleic acid.

27. A method of probing a nucleic acid array, said method comprising the steps of contacting said array with a probe of claim 25 and detecting signal from said detectable marker.

28. A composition comprising the formula:

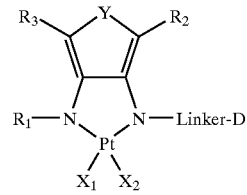

wherein:

—Y is selected from the group consisting of O, S, and C;

$R_1$–$R_3$ may be the same or different and are independently selected from the group consisting of H, methyl, benzyl, sulfonate, phosphonate, $NO_2$, $CF_3$, halogen, O—$R_4$, —(C=O)O$R_4$, or —OCH$_2$(C=O)$R_4$ and a salt, wherein $R_4$ is a straight or branched, saturated or unsaturated, substituted or unsubstituted alkyl having 1–10 carbons;

$X_1$ and $X_2$ are the same or different and at least one of $X_1$ or $X_2$ is a leaving group; and linker is a moiety joining a nitrogen to a detectable marker, D.

29. The composition of claim 28, wherein said leaving group is selected from the group consisting of $NO_3$, halogen, CN, OCOR$_5$, OCO-Phenyl, OCOCH$_2$OC(Phenyl)$_3$, O-Trityl and 3,5-dimethyl-phenyl-4-sulfate wherein $R_5$ is selected from the group consisting of H, methyl, benzyl, sulfonate, phosphonate, $NO_2$, $CF_3$, halogen, O—$R_4$, —(C=O)O$R_4$, —OCH$_2$(C=O)$R_4$ and a salt.

30. The composition of claim 28 wherein said linker is selected from the group consisting of: $(CH_2)n$, $(CH_2)_n$ $(CH=CH)_mO(CH=CH)_p(CH_2)_q$, $CO(CH_2)_n(CH=CH)_m$ $(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NEOSO, wherein

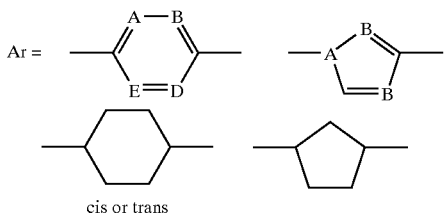

Ar = cis or trans and A, B, D, and E are the same or different and are selected from the group consisting of OH, N, O and S.

31. The composition of claim 28 wherein said detectable marker, D, is selected from the group consisting of a fluorophore, a chromophore, a radiolabel, an enzyme and an affinity tag.

32. A nucleic acid comprising a composition of claim 28.

33. The nucleic acid of claim 32 wherein said composition forms a non-covalent adduct with said nucleic acid.

34. A probe comprising a composition of claim 28.

35. A method of labeling a nucleic acid, said method comprising the step of contacting a composition of claim 28 with said nucleic acid.

36. A method of probing a nucleic acid array, said method comprising the steps of contacting said array with a probe of claim 34 and detecting signal from said detectable marker.

37. A composition comprising the formula:

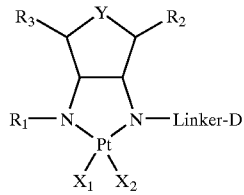

wherein:

Y is selected from the group consisting of O, S, and C;

$R_1$–$R_3$ may be the same or different and are independently selected from the group consisting of H, methyl, benzyl, sulfonate, phosphonate, $NO_2$, $CF_3$, halogen, O—$R_4$, —(C=O)$R_4$, or —OCH$_2$(C=O)$R_4$ and a salt, wherein $R_4$ is a straight or branched, saturated or unsaturated, substituted or unsubstituted alkyl having 1–10 carbons;

$X_1$ and $X_2$ are the same or different and at least one of $X_1$ or $X_2$ is a leaving group; and linker is a moiety joining a nitrogen to a detectable marker, D.

38. The composition of claim 37, wherein said leaving group is selected from the group consisting of $No_3$, halogen, CN, OCOR$_5$, OCO-Phenyl, OCOCH$_2$OC(Phenyl)$_3$, O-Trityl and 3,5-dimethyl-phenyl-4-sulfate, wherein $R_5$ is selected from the group consisting of H, methyl, benzyl, sulfonate, phosphonate, $NO_2$, $CF_3$, halogen, O—$R_4$, —(C=O)$R_4$, —OCH$_2$(C=O)$R_4$ and a salt.

39. The composition of claim 37 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

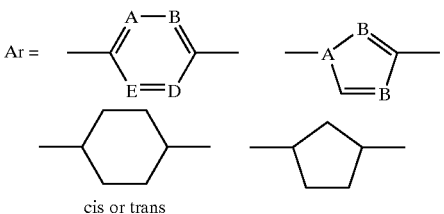

Ar = cis or trans and A, B, D, and E are the same or different and are selected from the group consisting of CH, N, O and S.

40. The composition of claim 37 wherein said detectable marker, D, is selected from the group consisting of a fluorophore, a chromophore, a radiolabel, an enzyme and an affinity tag.

41. A nucleic acid comprising a composition of claim 37.

42. The nucleic acid of claim 41 wherein said composition forms a non-covalent adduct with said nucleic acid.

43. A probe comprising a composition of claim 37.

44. A method of labeling a nucleic acid, said method comprising the step of contacting a composition of claim 37 with said nucleic acid.

45. A method of probing a nucleic acid array, said method comprising the steps of contacting said array with a probe of claim 43 and detecting signal from said detectable marker.

46. A composition comprising the formula

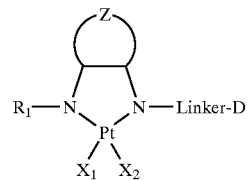

wherein

Z is selected from the group consisting of $(CH_2)n$, and $(CH_2)nO(CH_2)m$, wherein m and n are integers from 2 to 8, inclusive;

$R_1$ is selected from the group consisting of H, methyl, benzyl, sulfonate, phosphonate, $NO_2$, $CF_3$, halogen, O—$R_2$, —(C=O)$R_2$, or —OCH$_2$(C=O)$R_2$ and a salt, wherein $R_2$ is a straight or branched, saturated or unsaturated, substituted or unsubstituted alkyl having 1–10 carbons; $X_1$ and $X_2$ are the same or different and at least one of $X_1$ and $X_2$ is a leaving group; and linker is a moiety joining a nitrogen to a detectable marker, D.

47. The composition of claim 46, wherein said leaving group is selected from the group consisting of $No_3$, halogen, CN, OCOR$_3$, OCO-Phenyl, OCOCH$_2$OC(Phenyl)$_3$, O-Trityl and 3,5-dimethyl-phenyl-4-sulfate, wherein $R_3$ is selected from the group consisting of H, methyl, benzyl, sulfonate, phosphonate, $NO_2$, $CF_3$, halogen, O—$R_2$, —(C=O)$R_2$, —OCH$_2$(C=O)$R_2$ and a salt.

48. The composition of claim 46 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein Ar = 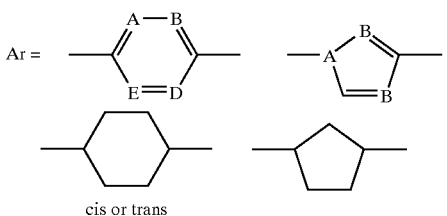

cis or trans and A, B, D, and E are the same or different and are selected from the group consisting of CH, N, O and S.

49. The composition of claim 46 wherein said detectable marker, D, is selected from the group consisting of a fluorophore, a chromophore, a radiolabel, an enzyme and an affinity tag.

50. A nucleic acid comprising a composition of claim 46.

51. The nucleic acid of claim 50 wherein said composition forms a non-covalent adduct with said nucleic acid.

52. A probe comprising a composition of claim 46.

53. A method of labeling a nucleic acid, said method comprising the step of contacting a composition of claim 46 with said nucleic acid.

54. A method of probing a nucleic acid array, said method comprising the steps of contacting said array with a probe of claim 52 and detecting signal from said detectable marker.

55. A composition comprising the formula

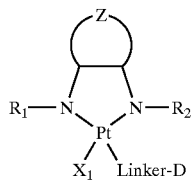

wherein

Z is selected from the group consisting of $(CH_2)_n$, and $(CH_2)_nO(CH_2)_m$, wherein m and n are integers from 2 to 8, inclusive;

$R_1$ and $R_2$ may be the same or different and are selected from the group consisting of H, methyl, benzyl, sulfonate, phosphonate, $NO_2$, $CF_3$, halogen, O—$R_3$, —(C=O)O$R_3$, or —OCH$_2$(C=O)$R_3$ and a salt, wherein $R_3$ is a straight or branched, saturated or unsaturated, substituted or unsubstituted alkyl having 1–10 carbons;

X is a leaving group; and linker is a moiety joining a detectable marker, D to the platinum ion.

56. The composition of claim 55, wherein said leaving group is selected from the group consisting of $NO_3$, halogen, CN, OCOR$_4$, OCO-Phenyl, OCOCH$_2$OC(Phenyl)$_3$, O-Trityl and 3,5-dimethyl-phenyl-4-sulfate, wherein $R_4$ is selected from the group consisting of H, methyl, benzyl, sulfonate, phosphonate, $NO_2$, $CF_3$, halogen, O—$R_3$, —(CO)O$R_3$, —OCH$_2$(C=O)$R_3$ and a salt.

57. The composition of claim 55 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein Ar = 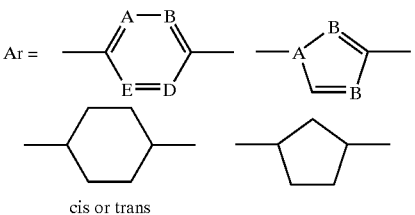

cis or trans and A, B, D, and E are the same or different and are selected from the group consisting of CH, N, O and S.

58. The composition of claim 55 wherein said detectable marker, D, is selected from the group consisting of a fluorophore, a chromophore, a radiolabel, an enzyme and an affinity tag.

59. A nucleic acid comprising a composition of claim 55.

60. The nucleic acid of claim 59 wherein said composition forms a non-covalent adduct with said nucleic acid.

61. A probe comprising a composition of claim 55.

62. A method of labeling a nucleic acid, said method comprising the step of contacting a composition of claim 55 with said nucleic acid.

63. A method of probing a nucleic acid array, said method comprising the steps of contacting said array with a probe of claim 61 and detecting signal from said detectable marker.

64. A composition comprising the formula:

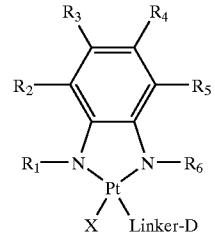

wherein:

$R_1$–$R_6$ may be the same or different and are independently selected from the group consisting of H, methyl, benzyl, sulfonate, phosphonate, $NO_2$, $CF_3$, halogen, O—$R_7$, —(C=O)O$R_7$, or —OCH$_2$(C=O)$R_7$ and a salt, wherein $R_7$ is a straight or branched, saturated or unsaturated, substituted or unsubstituted alkyl having 1–10 carbons;

X is a leaving group; and linker is a moiety joining a detectable marker, D to the platinum ion.

65. The composition of claim 64, wherein said leaving group is selected from the group consisting of $NO_3$, halogen, CN, OCOR$_8$, OCO-Phenyl, OCOCH$_2$OC(Phenyl)$_3$, O-Trityl and 3,5-dimethyl-phenyl-4-sulfate, wherein $R_8$ is selected from the group consisting of H, methyl, benzyl, sulfonate, phosphonate, $NO_2$, CE$_3$, halogen, O—$R_7$, —(C=O)O$R_6$, —OCH$_2$(C=O)$R_7$ and a salt.

66. The composition of claim 64 wherein said linker is selected from the group consisting of: $(CH_2)n$, $(CH_2)_n(CH=CH)_mO(CH=CH)_p(CH_2)_q$, $CO(CH_2)_n(CH=CH)_m(CH_2)_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NBCSNH, NHCSO, wherein Ar = 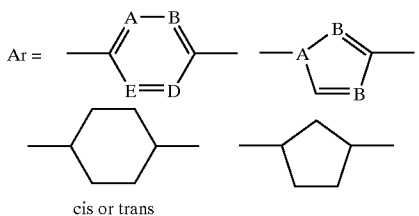

cis or trans and A, B, D, and E are the same or different and are selected from the group consisting of CH, N, O and S.

67. The composition of claim 64 wherein the detectable marker, D, is selected from the group consisting of a fluorophore, a chromophore, a radiolabel, an enzyme and an affinity tag.

68. A nucleic acid comprising a composition of claim 64.

69. The nucleic acid of claim 68 wherein said composition forms a non-covalent adduct with said nucleic acid.

70. A probe comprising a composition of claim 64.

71. A method of labeling a nucleic acid, said method comprising the step of contacting a composition of claim 67 with said nucleic acid.

72. A method of probing a nucleic acid array, said method comprising the steps of contacting said array with a probe of claim 70 and detecting signal from said detectable marker.

73. A composition comprising the formula

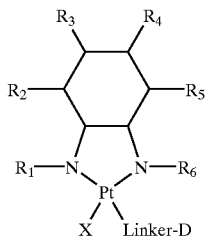

wherein $R_1$–$R_6$ may be the same or different and are independently selected from the group consisting of H, methyl, benzyl, sulfonate, phosphonate, $NO_2$, $CF_3$, halogen, O—$R_7$, —(C=O)O$R_7$, or —OCH$_2$(C=O)$R_7$ and a salt, wherein $R_7$ is a straight or branched, saturated or unsaturated, substituted or unsubstituted alkyl having 1–10 carbons;

X is a leaving group; and linker is a moiety joining a detectable marker, D, to the platinum ion.

74. The composition of claim 73, wherein said leaving group is selected from the group consisting of $NO_3$, halogen, CN, OCO$R_8$, OCO-Phenyl, OCOCH$_2$OC(Phenyl)$_3$, O-Trityl and 3,5-dimethyl-phenyl-4-sulfate, wherein $R_8$ is selected from the group consisting of H, methyl, benzyl, sulfonate, phosphonate, $NO_2$, $CF_3$, halogen, O—$R_7$, —(C=O)O$R_6$, —OCH$_2$(C=O)$R_7$ and a salt.

75. The composition of claim 73 wherein said linker is selected from the group consisting of: $(CH_2)n$, $(CH_2)_n$ (CH=CH)$_m$O(CH=CH)$_p$(CH$_2$)$_q$, CO(CH$_2$)$_n$(CH=CH)$_m$ (CH$_2$)$_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNB, NHCSO, wherein Ar = 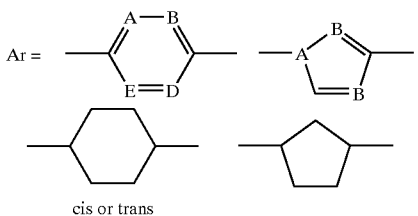

cis or trans and A, B, D, and E are the same or different and are selected from the group consisting of CH, N, O and S.

76. The composition of claim 73 wherein the detectable marker, D, is selected from the group consisting of a fluorophore, a chromophore, a radiolabel, an enzyme and an affinity tag.

77. A nucleic acid comprising a composition of claim 73.

78. The nucleic acid of claim 77 wherein said composition forms a non-covalent adduct with said nucleic acid.

79. A probe comprising a composition of claim 73.

80. A method of labeling a nucleic acid, said method comprising the step of contacting a composition of claim 73 with said nucleic acid.

81. A method of probing a nucleic acid array, said method comprising the steps of contacting said array with a probe of claim 79 and detecting signal from said detectable marker.

82. A composition comprising the formula:

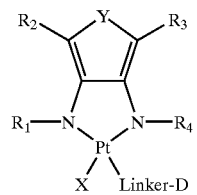

wherein

Y is selected from the group consisting of O, S, and C;

$R_1$–$R_4$ may be the same or different and are independently selected from the group consisting of H, methyl, benzyl, sulfonate, phosphonate, $NO_2$, $CF_3$, halogen, O—$R_5$, —(C=O)O$R_5$, or —OCH$_2$(C=O)$R_5$ and a salt, wherein $R_5$ is a straight or branched, saturated or unsaturated, substituted or unsubstituted alkyl having 1–10 carbons;

X is a leaving group; and linker is a moiety joining a detectable marker, D, to the platinum ion.

83. The composition of claim 82 wherein said leaving group is selected from the group consisting of $NO_3$, halogen, CN, OCO$R_6$, OCO-Phenyl, OCOCH$_2$OC(Phenyl)$_3$, O-Trityl and 3,5-dimethyl-phenyl-4-sulfate, wherein $R_6$ is selected from the group consisting of H, methyl, benzyl, sulfonate, phosphonate, $NO_2$, $CF_3$, halogen, O—$R_5$, —(C=O)O$R_5$, —OCH$_2$(C=O)$R_5$ and a salt.

84. The composition of claim 82 wherein said linker is selected from the group consisting of: $(CH_2)n$, $(CH_2)_n$ (CH=CH)$_m$O(CH=CH)$_p$(CH$_2$)$_q$, CO(CH$_2$)$_n$(CH=CH)$_m$ (CH$_2$)$_p$, COAr(CH$_2$)$_n$(CH=CH)$_m$(CH$_2$)$_p$, NH$_2$(CH$_2$)$_n$Q, NH$_2$((CH$_2$)$_n$O)$_m$(CH$_2$)$_t$Q, NH$_2$(CH$_2$)$_m$Ar(CH$_2$)$_n$Q, wherein m, n, p, q and t are integers from 0 to 8, inclusive, and m, n, p, q and t are the same or different, wherein Q is selected from the group consisting of CONH, NHCO, —S—S—, NHCSNH, NHCSO, wherein

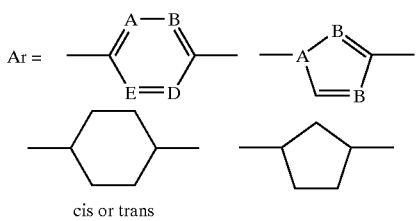

cis or trans and A, B, D, and E are the same or different and are selected from the group consisting of CH, N, O and S.

85. The composition of claim 82 herein the detectable marker, D, is selected from the group consisting of a fluorophore, a chromophore, a radiolabel, an enzyme and an affinity tag.

86. nucleic acid comprising a composition of claim 82.

87. The nucleic acid of claim 86 wherein said composition forms a non-covalent adduct with said nucleic acid.

88. A probe comprising a composition of claim 82.

89. A method of labeling a nucleic acid, said method comprising the step of contacting a composition of claim 82 with said nucleic acid.

90. A method of probing a nucleic acid array, said method comprising the steps of contacting said array with a probe of claim 88 and detecting signal from said detectable marker.

91. A composition comprising the formula:

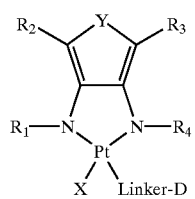

wherein

Y is selected from the group consisting of O, S, and C;

$R_1$–$R_4$ may be the same or different and are independently selected from the group consisting of H, methyl, benzyl, sulfonate, phosphonate, $NO_2$, $CF_3$, halogen, O—$R_5$, —(C=O)O$R_5$, or —O$CH_2$(C=O)$R_5$ and a salt, wherein $R_5$ is a straight or branched, saturated or unsaturated, substituted or unsubstituted alkyl having 1–10 carbons;

X is a leaving group; and linker is a moiety joining a detectable marker, D, to the platinum ion.

92. The composition of claim 91, wherein said leaving group is selected from the group consisting of $NO_3$, halogen, CN, OCO$R_6$, OCO-Phenyl, OCOCH$_2$OC(Phenyl)$_3$, O-Trityl and 3,5-dimethyl-phenyl-4-sulfate, wherein $R_6$ is selected from the group consisting of H, methyl, benzyl, sulfonate, phosphonate, $NO_2$, $CF_3$, halogen, O—$R_5$, —(C=O)O$R_5$, —OCH$_2$(C=O)$R_5$ and a salt.

93. The composition of claim 91 wherein said linker is selected from the group consisting of: $(CH_2)n$, $(CH_2)_n(CH=CH)_m O(CH=CH)_p(CH_2)_q$, $CO(CH_2)_n(CH=CH)_m(CH_2)_p$, $COAr(CH_2)_n(CH=CH)_m(CH_2)_p$, $NH_2(CH_2)_nQ$, $NH_2((CH_2)_nO)_m(CH_2)_tQ$, $NH_2(CH_2)_mAr(CH_2)_nQ$, wherein m, n, p, q and t are integers from 0 to 8, inclusive, and m, n, p, q and t are the same or different, wherein Q is selected from the group consisting of CONH, NIICO, —S—S—, NHCSNH, NHCSO, wherein

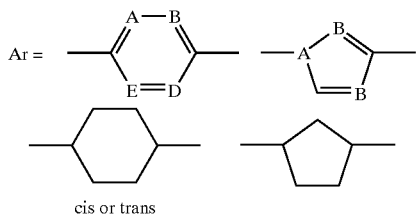

cis or trans and A, B, D, and E are the same or different and are selected from the group consisting of CH, N, O and S.

94. The composition of claim 91 wherein the detectable marker, D, is selected from the group consisting of a fluorophore, a chrornophore, a radiolabel, an enzyme and an affinity tag.

95. A nucleic acid comprising a composition of claim 91.

96. The nucleic acid of claim 95 wherein said composition forms a non-covalent adduct with said nucleic acid.

97. A probe comprising a composition of claim 91.

98. A method of labeling a nucleic acid, said method comprising the step of contacting a composition of claim 91 with said nucleic acid.

99. A method of probing a nucleic acid array, said method comprising the steps of contacting said array with a probe of claim 97 and detecting signal from said detectable marker.

100. A method of making a platinum labeling compound that comprises a stabilizing bridge, the method comprising the step of contacting potassium tetrachloroplatinate (II) with a cycloaliphatic diamine labeled with a detectable marker, wherein said contacting results in a cis-platinum dichloride labeling compound.

101. The method of claim 100 wherein said cycloaliphatic diamine is a 1,2-cycloaliphatic diamine.

102. The method of claim 100 wherein said cycloaliphatic diamine is a cyclohexyl diamine.

103. The method of claim 102 wherein said cyclohexyl diamine is a 1,2-cyclohexyl diamine.

104. The method of claim 100 wherein said contacting is performed in aqueous solution at a pH of about 1.5 to 5.5 and at a temperature of about 65° C.

* * * * *